United States Patent
Baar et al.

(10) Patent No.: US 11,312,695 B2
(45) Date of Patent: Apr. 26, 2022

(54) NUTRIENTS TO ENHANCE LOAD-INDUCED MUSCLE HYPERTROPHY

(71) Applicants: The Regents of the University of California, Oakland, CA (US); University of Birmingham, Birmingham (GB)

(72) Inventors: Keith Baar, Davis, CA (US); Andrew Philp, Darlinghurst (AU); Simon Schenk, La Jolla, CA (US)

(73) Assignees: The Regents of the University of California, Oakland, CA (US); University of Birmingham, Birmingham (GB)

(*) Notice: Subject to any disclaimer, the term of this patent is extended or adjusted under 35 U.S.C. 154(b) by 0 days.

(21) Appl. No.: 17/183,252

(22) Filed: Feb. 23, 2021

(65) Prior Publication Data
US 2021/0214329 A1 Jul. 15, 2021

Related U.S. Application Data

(63) Continuation of application No. PCT/US2021/013613, filed on Jan. 15, 2021.

(60) Provisional application No. 62/987,807, filed on Mar. 10, 2020.

(51) Int. Cl.
*C07D 311/04* (2006.01)
*A23L 33/10* (2016.01)

(52) U.S. Cl.
CPC ............ *C07D 311/04* (2013.01); *A23L 33/10* (2016.08)

(58) Field of Classification Search
CPC .............................. C07D 311/04; A23L 33/10
See application file for complete search history.

(56) References Cited

U.S. PATENT DOCUMENTS

| 9,480,675 B2 | 11/2016 | Philp et al. |
| 2015/0025052 A1 | 1/2015 | Chadli et al. |
| 2016/0038457 A1* | 2/2016 | Garvey ................... A61P 43/00 514/456 |

FOREIGN PATENT DOCUMENTS

| JP | 2015 012986 A | 1/2015 |
| JP | 2016 199536 A | 12/2016 |
| KR | 2012097705 | * 9/2012 |
| KR | 101692081 B1 | 1/2017 |
| WO | 2013/142816 A1 | 9/2013 |
| WO | WO 2013/142816 | * 9/2013 |
| WO | 2015/094772 A1 | 6/2015 |
| WO | 2018/166404 A1 | 9/2018 |
| WO | 2021/072450 A3 | 4/2021 |

OTHER PUBLICATIONS

Epigallocatechin gallate at https://en.wikipedia.org/ wiki/ Epigallocatechin_gallate (retrieved from the internet Aug. 5, 2021) (Year: 2021).*

Human Body Weight at https://en.wikipedia.org /wiki/Human_body_ weight (retrieved from the internet Aug. 5, 2021) (Year: 2021).*

Baar et al. "Phosphorylation of $p70^{S6k}$ correlates with increased skeletal muscle mass following resistance exercise", Am J Physiol, 1999, pp. C120-C127.

Celis-Morales et al. "Associations of grip strength with cardiovascular, respiratory, and cancer outcomes and all cause mortality: prospective cohort study of half a million UK Biobank participants", May 8, 2018, doi: 10.1136/bmj.k1651, pp. 1-10.

Cermak et al. "Protein supplementation augments the adaptive response of skeletal muscle to resistance-type exercise training: a meta-analysis". Am J Clin Nutr 2012, 96, pp. 1454-1464.

Choudhary et al. "Lysine Acetylation Targets Protein Complexes and Co-Regulates Major Cellular Functions", Science Express, Jul. 16, 2009. science.sciencemag.org/.

Das et al. "Deacetylation of S6 kinase promotes high glucose-induced glomerular mesangial cell hypertrophy and matrix protein accumulation", J. Biol. Chem., 2019, 294(24), pp. 9440-9460.

Fenton et al. "S6K1 is acetylated at lysine 516 in response to growth factor stimulation", Biochem Biophys Res Commun, 2010, 398, pp. 400-405.

Fenton et al. "Histone acetyltransferases interact with and acetylate p70 ribosomal S6 kinases in vitro and in vivo", Int J Biochem Cell Biol, 2010, 42, pp. 359-366.

Figueiredo et al. "Regulation of Ribosome Biogenesis in Skeletal Muscle Hypertrophy", Int. Union Physiol. Sci./Am. Physiol. Soc., Jan. 2019, pp. 30-42.

Hong et al. "Cross-talk between Sirtuin and Mammalian Target of Rapamycin Complex 1 (mTORC1) Signaling in the Regulation of S6 Kinase 1 (S6K1) Phosphorylation", The Journal of Biological Chemistry, May 9, 2014, vol. 289, No. 19, pp. 13132-13141.

Jorgenson et al. "The overlooked role of fiber length in mechanical load-induced growth of skeletal muscle", Exerc Sport Sci Rev, Oct. 2019, 47 (4), 258-259.

Kirby et al. "Blunted hypertrophic response in aged skeletal muscle is associated with decreased ribosome biogenesis", J Appl Physiol, 2015, 119, pp. 321-327.

(Continued)

*Primary Examiner* — Marcos L Sznaidman
(74) *Attorney, Agent, or Firm* — Kilpatrick Townsend & Stockton LLP

(57) ABSTRACT

Methods and compositions are provided for increasing muscle hypertrophy, e.g., through the administration of novel combinations of natural products that inhibit SIRT1.

14 Claims, 13 Drawing Sheets

Specification includes a Sequence Listing.

(56) References Cited

OTHER PUBLICATIONS

Liew et al. "Acetylation of Ribosomal Proteins: Characterization and Properties of Rat Liver Ribosomal Proteins", Journal of Biological Chemistry, Feb. 10, 1973, vol. 248, No. 3, pp. 977-983.
Pandey et al. "Plant polyphenols as dietary antioxidants in human health and disease", Oxid Med Cell Longevity, vol. 2, Issue 5, pp. 270-278.
Rantanen et al., "Muscle Strength and Body Mass Index as Long-Term Predictors of Mortality in Initially Healthy Men", Journal of Gerontology, 2000, vol. 55S, No. 3, pp. M168-M173.
Ruiz et al. "Association between muscular strength and mortality in men prospective cohort study", Br Med J, Jul. 12, 2008, vol. 337, pp. 92-95.
Solomon et al. "Inhibition of SIRT1 Catalytic Activity Increases p53 Acetylation but Does Not Alter Cell Survival following DNA Damage", Mol Cell Biol, Jan. 2006, vol. 26, pp. 28-38.
Srikanthan et al. "Muscle Mass Index as a Predictor of Longevity in Older Adults", Am J Med, Jun. 2014, vol. 127, No. 6, pp. 547-553.
Stec et al. "Ribosome biogenesis may augment resistance training-induced myofiber hypertrophy and is required for myotube growth in vitro", Am J Physiol Endocrinol Metab Apr. 15, 2016, vol. 310, No. 8, pp. E652-E661.
Yang et al. "NAD+-dependent Deacetylase SIRT3 Regulates Mitochondrial Protein Synthesis by Deacetylation of the Ribosomal Protein MRPL10" The Journal of Biological Chemistry, Mar. 5, 2010, vol. 285, No. 10, pp. 7417-7429.

* cited by examiner

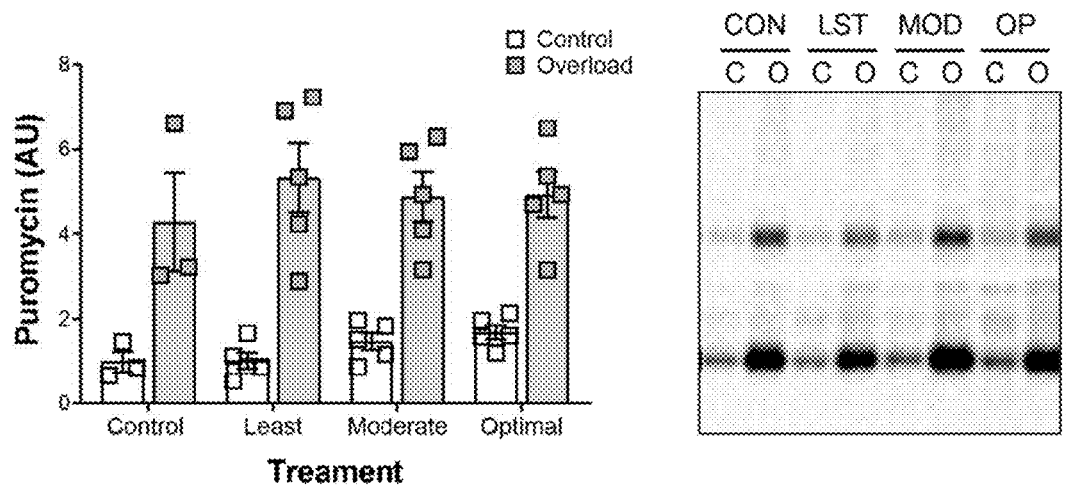
FIG. 4A
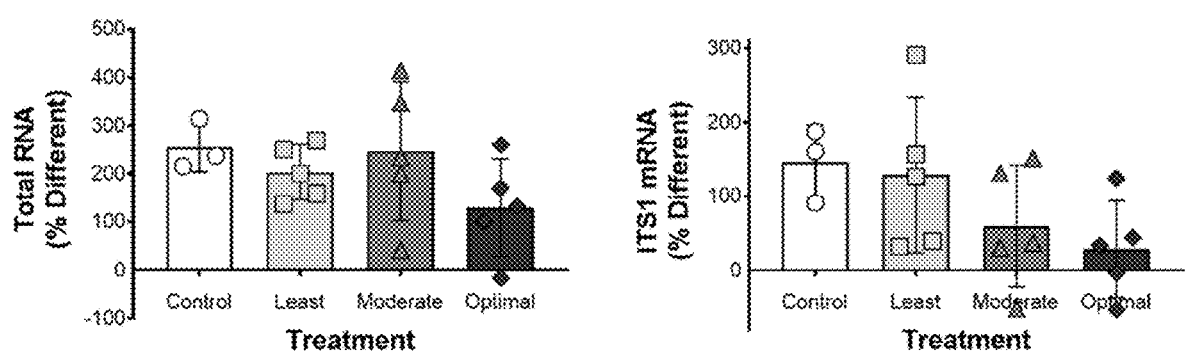
FIG. 4B
FIG. 4C

NUTRIENTS TO ENHANCE LOAD-INDUCED MUSCLE HYPERTROPHY

CROSS REFERENCE TO RELATED APPLICATIONS

The present application is a continuation of International Pat. Appl. Ser. No. PCT/US2021/013613, filed on Jan. 15, 2021, which application claims priority to U.S. Provisional Pat. Appl. No. 62/987,807, filed on Mar. 10, 2020, the contents of which are incorporated herein by reference in their entirety for all purposes.

SEQUENCE LISTING

The instant application contains a Sequence Listing which has been submitted electronically in ASCII format and is hereby incorporated by reference in its entirety. Said ASCII copy, created on Mar. 24, 2021, is named 070772-228610US-1233699_SL.txt and is 1,301 bytes in size.

BACKGROUND

Muscle mass and strength are important aspects of human health, since the rate of mortality of individuals correlates with both low muscle mass (17) and strength (14, 15). Low muscle mass and function also limit post-surgery recovery and mobility and increase the impact or risk of diseases such as diabetes, cardiovascular disease, and cancer (2). Thus, improving muscle mass and strength is a vital part of a long life (8).

Muscle mass and strength are also important components of human aesthetics and performance. Each year, large amounts of money are spent on supplements that are purported to result in increases in muscle mass and strength. Many of these products are of dubious scientific value, since wide scale screens for products that result in bona fide improvements in muscle mass and strength are rare. One clinically validated way to increase muscle mass gains as a result of training is to combine strength training with protein supplementation (3). However, very few other scientifically validated nutritional ways to increase muscle mass in response to training have been reported.

Sirtuin1 (SIRT1) is an $NAD_+$-dependent deacetylase that is activated in muscle in response to changes in cellular energy flux. Metabolic stress during calorie restriction (6) and endurance exercise (3) are known to directly activate SIRT1. Since calorie restriction as well as endurance exercise are also known to slow muscle growth (1, 7), we hypothesized that SIRT1 inhibits muscle growth. Protein acetylation has also been linked to muscle growth. The ribosomal S6 protein kinase (S6K1), whose phosphorylation and activity have previously been shown to be associated with increased muscle protein synthesis and muscle hypertrophy (1), can be acetylated by the acetyl transferase p300 and deacetylated by SIRT1 (9). Beyond S6K1, almost every protein within the ribosome is regulated by acetylation (4). These data suggest that acetylation may be a novel way to regulate protein synthesis. Since loading and nutrition result in transient increases in muscle protein synthesis that are thought to play an important role in muscle growth, we sought to determine whether altering acetylation could augment the increase in muscle fiber cross sectional area in response to a hypertrophy stimulus.

There is therefore a need in the art for new, scientifically valid, effective, and safe methods and compositions for promoting muscle hypertrophy and increasing muscle mass and strength. The present disclosure satisfies this need and provides other advantages as well.

BRIEF SUMMARY

In one aspect, the present disclosure provides a method of enhancing skeletal muscle growth in a mammal undergoing muscle loading, comprising administering to the mammal a composition comprising therapeutically effective amounts of (i) one or more catechins, and (ii) celastrol or a derivative thereof.

In some embodiments, the one or more catechins comprise epicatechin or epigallocatechin-3-monogallate. In some embodiments, the one or more catechins comprise epicatechin and epigallocatechin-3-monogallate. In some embodiments, the celastrol derivative is dihydrocelastrol. In some embodiments, the composition comprises epicatechin, epigallocatechin-3-monogallate, and celastrol. In some embodiments, the composition results in an increase in the muscle fiber cross-sectional area of at least one skeletal muscle in the mammal. In some embodiments, the composition does not substantially alter the body mass or the heart or liver weight of the mammal. In some embodiments, the composition reduces the activity of SIRT1 in one or more muscles of the mammal. In some embodiments, the composition increases the acetylation of one or more ribosomal proteins in one or more muscles of the mammal.

In some embodiments, the composition is orally administered to the mammal. In some embodiments, the composition is formulated as a nutritional supplement or food additive. In some embodiments, the nutritional supplement or food additive is a pill, tablet, capsule, liquid, powder, energy bar, protein bar, or gummy. In some embodiments, the mammal is a human. In some embodiments, the composition is formulated and administered such that the mammal receives about 0.7-1.3 mg/kg/day of epicatechin. In some embodiments, the composition is formulated and administered such that the mammal receives about 0.7 mg/kg/day of epicatechin. In some embodiments, the composition is formulated and administered such that the mammal receives about 6-20 mg/kg/day of epigallocatechin-3-monogallate. In some embodiments, the composition is formulated and administered such that the mammal receives about 20 mg/kg/day of epigallocatechin-3-monogallate. In some embodiments, the composition is formulated and administered such that the mammal receives about 0.2-0.5 mg/kg/day of celastrol. In some embodiments, the composition is formulated and administered such that the mammal receives about 0.5 mg/kg/day of celastrol. In some embodiments, the composition is formulated and administered such that the mammal receives about 0.7 mg/kg/day of epicatechin, about 20 mg/kg/day of epigallocatechin-3-monogallate, and about 0.5 mg/kg/day of celastrol. In some embodiments, the composition is formulated and administered such that the relative weight ratio of the epitatechin, epigallocatechin-3-monogallate, and celastrol received by the mammal is about 0.7:20:0.5, respectively. In some embodiments, the composition is formulated and administered such that the relative mole ratio of the epitatechin, epigallocatechin-3-monogallate, and celastrol received by the mammal is about 1.6:43.6:1.1, respectively. In some embodiments, the method further comprises increasing the caloric intake and/or the intake of muscle growth promoting amino acids in the mammal concomitant to the muscle loading and administration of the composition. In some embodiments, the composition further comprises leucine, branched-chain amino acids, or protein with high leucine content.

In another aspect, the present disclosure provides a composition for enhancing muscle growth in a mammal undergoing muscle loading, the composition comprising therapeutically effective amounts of (i) one or more catechins, and (ii) celastrol or a derivative thereof.

In some embodiments, the one or more catechins comprise epicatechin or epigallocatechin-3-monogallate. In some embodiments, the one or more catechins comprise epicatechin and epigallocatechin-3-monogallate. In some embodiments, the celastrol derivative is dihydrocelastrol. In some embodiments, the composition comprises epicatechin, epigallocatechin-3-monogallate, and celastrol. In some embodiments, the composition is formulated for oral administration. In some embodiments, the composition is formulated as a nutritional supplement or food additive. In some embodiments, the nutritional supplement or food additive is a pill, tablet, capsule, liquid, powder, energy bar, protein bar, or gummy. In some embodiments, the composition further comprises leucine, branched-chain amino acids, or protein with high leucine content.

In some embodiments, the composition is formulated such that the mammal receives about 0.7-1.3 mg/kg/day of epicatechin. In some embodiments, the composition is formulated such that the mammal receives about 0.7 mg/kg/day of epicatechin. In some embodiments, the composition is formulated such that the mammal receives about 6-20 mg/kg/day of epigallocatechin-3-monogallate. In some embodiments, the composition is formulated such that the mammal receives about 20 mg/kg/day of epigallocatechin-3-monogallate. In some embodiments, the composition is formulated such that the mammal receives about 0.2-0.5 mg/kg/day of celastrol. In some embodiments, the composition is formulated such that the mammal receives about 0.5 mg/kg/day of celastrol. In some embodiments, the composition is formulated such that the mammal receives about 0.7 mg/kg/day of epicatechin, about 20 mg/kg/day of epigallocatechin-3-monogallate, and about 0.5 mg/kg/day of celastrol. In some embodiments, the relative weight ratio of the epicatechin, epigallocatechin-3-monogallate, and celastrol in the composition is about 0.7:20:0.5, respectively. In some embodiments, the relative mole ratio of the epicatechin, epigallocatechin-3-monogallate, and celastrol in the composition is about 1.6:43.6:1.1, respectively.

Other objects, features, and advantages of the present disclosure will be apparent to one of skill in the art from the following detailed description and figures.

BRIEF DESCRIPTION OF THE DRAWINGS

FIG. 1A: Mean change in fiber cross-sectional area for each of the 18 different treatment groups following 14 days of overload. FIG. 1B: Response surface plot for the relationship between CSA and the amount of epicatechin and epigallocatechin-3-gallate at a constant level of celastrol (500 µg/kg/day).

(FIG. 2A) Body weight, (FIG. 2B) heart weight/body weight, (FIG. 2C) liver weight/body weight, (FIG. 2D) muscle mass following 14 days of overload with different levels of natural products. FIG. 2E: Distributions of fiber cross-sectional area changes in the control, least effective, moderately effective, and most effective combinations of natural products, from left to right. FIG. 2F: Relationship between muscle fiber CSA and muscle mass following 14 days of overload. Note that in this model muscle mass increases ~80% before a measurable change in mean fiber CSA occurs. FIG. 2G: Mean fiber CSA as a function of overload and treatment. FIG. 2H: Relationship between the prediction of the change in fiber CSA from the Box-Behnken model and the actual measured change in fiber CSA following 14 days of overload. Data are means±SEM for n=5 animals per treatment group. * indicates a significant difference from control muscle.

FIG. 3A: Levels of SIRT1 protein following overload and natural product treatment. FIG. 3B: Acetylation of p53 at K382 with both overload and treatment with natural products. Note the greater increase in p53 acetylation with the natural product treatment. However, the variability in each group precludes statistical significance. Finally, FIG. 3C shows the level of acetylation of lysines in the whole muscle homogenate. Data are means±SEM for n=5 animals per treatment group with every point shown. * indicates a significant difference from control muscle.

FIGS. 4A-4G. Protein synthesis and ribosomal markers with overload and natural product treatment. FIG. 4A: Protein synthesis as estimated by SUnSET. Both the blot and quantified data are shown. Estimates of ribosomal mass were made by measuring (FIG. 4B) total RNA (~80% of which is ribosomal RNA), (FIG. 4C) the internal transcribed spacer 1 (ITS1), and (FIG. 4D) the 5' external transcribed spacer (5'ETS). To get an idea of Akt-mTORC1 signaling, (FIG. 4E) Akt Ser473, (FIG. 4F) S6K1 Thr389, and (FIG. 4G) eEF2 phosphorylation were measured. Data are means±SEM for n=5 animals per treatment group with every point shown. * indicates a significant difference from control muscle.

(FIG. 5A) MuRF and (FIG. 5B) MaFBx mRNA were measured. Data are means±SEM for n=5 animals per treatment group with every point shown. * indicates a significant difference from control muscle.

FIG. 6C: Levels of S6K1 acetylation were also determined in the same manner. Note the opposite pattern of the two measures. Data are means±SEM for n=5 animals per treatment group with every point shown. * indicates a significant difference from control muscle.

DETAILED DESCRIPTION

1. Introduction

Figure 1A:
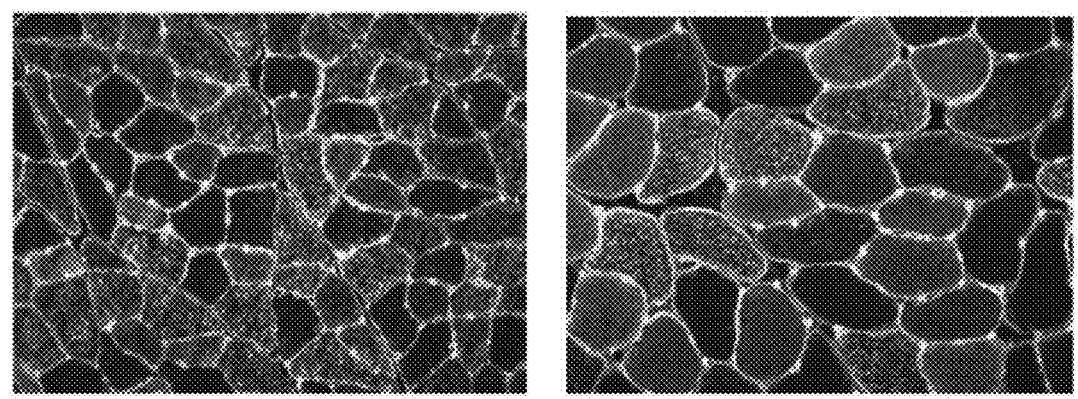
FIGS. 1A-1B. Development of a Box-Behnken model of natural products versus muscle cross-sectional area. Eighteen separate combinations and concentrations of the three natural products were studied using an incomplete factorial design. Thirteen of the combinations were unique, whereas five were identical in order to determine the biological variability in the system.

The present disclosure provides methods and compositions for enhancing loading-induced muscle hypertrophy in subjects. In particular, the present disclosure is based on the surprising discovery that certain natural products can be combined in specific ways to produce novel combinations that do not exist in nature and that can be used to safely and effectively enhance muscle hypertrophy in a subject, and thereby increase the mass and other features of skeletal muscles in the subject. The present methods and compositions can lead to substantial increases in muscle mass relative to muscles subjected to loading but not receiving the compositions. For example, adding the present combinations of natural products on top of a standardized loading program can lead to an increase in muscle mass that is at least 30% greater than the increase seen with loading alone. Without being bound by the following theory, it is believed that the present natural products inhibit the Sirtuin 1 protein (SIRT1), leading to increased acetylation of ribosomal and other proteins, to enhanced ribosomal function, and to enhanced muscle growth.

In some embodiments, the composition comprises a combination of natural compounds including one or more catechins as well as celastrol or a derivative thereof. In a particular embodiment, the compositions comprise celastrol, epicatechin, and epigallocatechin monogallate.

The herein-described natural products can be administered to a subject in any of a number of ways. In particular embodiments the natural products are administered orally, e.g., as a nutritional supplement or food additive. In some embodiments, the nutritional supplement or food additive is a pill, tablet, capsule, liquid, powder, energy bar, protein bar, or gummy. In particular embodiments, the natural products included in the combination are certified as generally recognized as safe (GRAS), meaning that they can be readily formulated for human consumption, e.g., as a food additive.

2. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" as used herein shall generally mean an acceptable degree of error for the quantity measured given the nature or precision of the measurements. Typically, exemplary degrees of error are within 20 percent (%), preferably within 10%, and more preferably within 5% of a given value or range of values. Any reference to "about X" specifically indicates at least the values X, 0.8X, 0.81X, 0.82X, 0.83X, 0.84X, 0.85X, 0.86X, 0.87X, 0.88X, 0.89X, 0.9X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, 1.1X, 1.11X, 1.12X, 1.13X, 1.14X, 1.15X, 1.16X, 1.17X, 1.18X, 1.19X, and 1.2X. Thus, "about X" is intended to teach and provide written description support for a claim limitation of, e.g., "0.98X."

The terms "expression" and "expressed" refer to the production of a transcriptional and/or translational product, e.g., of a nucleic acid sequence encoding a protein (e.g., SIRT1). In some embodiments, the term refers to the production of a transcriptional and/or translational product encoded by a gene (e.g., the human SIRT1 gene) or a portion thereof. The level of expression of a DNA molecule in a cell may be assessed on the basis of either the amount of corresponding mRNA that is present within the cell or the amount of protein encoded by that DNA produced by the cell.

As used herein, "catechin" refers to a family of flavanols, or flavan-3-ols, and derivatives thereof. Catechins are members of the family of flavonoids and are naturally present in, e.g., cocoa powder, chocolate, tea, and grapes. Catechins possess two benzene rings and a dihydropyran heterocycle with a hydroxyl group on carbon 3. Catechins have four diastereoisomers, two of which are in a trans configuration (referred to as "catechins") and two in a cis configuration (referred to as "epicatechins"). As used herein, the term "catechin" can refer generically to any type of catechin, including epicatechin, epigallocatechin, gallocatechin, and gallate derivatives of each of these. In some embodiments, the catechins included in the present compositions are epicatechins. An "epicatechin" as used herein refers to both diastereoisomers, i.e., (−)-epicatechin (see, e.g., PubChem CID 72276) or (+)-epicatechin (see, e.g., PubChem CID 182232), as well as derivatives thereof. For example, an "epicatechin" can refer to an epigallocatechin (see, e.g., PubChem CID 72277), a flavan-3,3',4',5,5',7-hexol, i.e., (−)-epigallocatechin or (+)-epigallocatechin, as well as esters of epicatechins or epigallocatechins and gallic acid, e.g., epigallocatechin gallate, epigallocatechin-3-gallate, epigallocatechin monogallate, epicatechin gallate, epicatechin monogallate, and others. In particular embodiments, the catechin is epicatechin gallate (or epicatechin monogallate) (see, e.g., PubChem CID 107905; mol. wt. 442.4 g/mol) and/or epigallocatechin gallate (or epigallocatechin monogallate, or epigallocatechin-3-gallate, or epigallocatechin-3-monogallate) (see, e.g., PubChem CID 65064; mol. wt. 458.4 g/mol).

As used herein, "celastrol" refers to a pentacyclic triterpenoid, originally isolated from *Tripterygium regelii*, with an exemplary structure as shown in PubChem CID 122724 (mol. wt. 450.6 g/mol). The present compositions also comprise celastrol derivatives, such as dihydrocelastrol (see, e.g., PubChem CID 10411574), a compound synthesized through the hydrogenation of celastrol.

"SIRT1" or "sirtuin 1" or "Silent Mating Type Information Regulation 2 Homolog 1" is a member of class 1 of the sirtuin family of proteins, which are homologs of the yeast Sir2 protein. SIRT1 is an $NAD^+$-dependent deacetylase and is activated in muscle in response to changes in cellular energy flux. SIRT1 can deacetylate proteins such as p53 and the ribosomal S6 protein kinase (S6K1). Information about the function, structure, localization, etc. of SIRT1 protein can be found, inter alia, at UniProt Q96EB6 (SIR1_HUMAN); the SIRT1 gene corresponds, e.g., to NCBI Gene ID No.: 23411.

A "SIRT1 inhibitor" refers to any agent, e.g., a natural product such as celastrol or a catechin such as epicatechin or epigallocatechin-3-monogallate, that is capable of inhibiting, reducing, decreasing, attenuating, abolishing, eliminating, slowing, or counteracting in any way any aspect of the expression, stability, or activity of SIRT1. A SIRT1 inhibitor can, for example, reduce any aspect of the expression, e.g., transcription, RNA processing, RNA stability, or translation of a gene encoding SIRT1, e.g., the human SIRT1 gene, by, e.g., 10%, 15%, 20%, 25%, 30%, 35%, 40%, 45%, 50%, 55%, 60%, 65%, 70%, 75%, 80%, 85%, 90%, 95%, or more as compared to a control, e.g., in the absence of the inhibitor, in vitro or in vivo. Similarly, a SIRT1 inhibitor can, for example, reduce the activity, e.g., enzymatic activity such as deacetylase activity on a substrate such as p53 or S6K1, of a SIRT1 enzyme by, e.g., 10%, 15%, 20%, 25%, 30%, 35%, 40%, 45%, 50%, 55%, 60%, 65%, 70%, 75%, 80%, 85%, 90%, 95%, or more as compared to a control, e.g., in the absence of the inhibitor, in vitro or in vivo. Further, a SIRT1 inhibitor can, for example, reduce the stability of a SIRT1 enzyme by, e.g., 10%, 15%, 20%, 25%, 30%, 35%, 40%, 45%, 50%, 55%, 60%, 65%, 70%, 75%, 80%, 85%, 90%, 95%, or more as compared to a control, e.g., in the absence of the inhibitor, in vitro or in vivo. In particular embodiments, a SIRT1 inhibitor is a natural product such as celastrol, a celastrol derivative, or a catechin or epicatechin such as epicatechin or epigallocatechin-3-monogallate.

The term "derivative," in the context of a compound, includes but is not limited to, amide, ether, ester, amino, carboxyl, acetyl, and/or alcohol derivatives of a given compound.

The term "administer," "administering," or "administration" refers to the methods that may be used to enable delivery of agents or compositions such as the compounds described herein to a desired site of biological action. These methods include, but are not limited to, parenteral administration (e.g., intravenous, subcutaneous, intraperitoneal, intramuscular, intra-arterial, intravascular, intracardiac, intrathecal, intranasal, intradermal, intravitreal, and the like), transmucosal injection, oral administration, administration as a suppository, and topical administration. In particular embodiments of the present disclosure, the compositions, e.g., combinations of SIRT1-inhibiting compounds, are natural products and are formulated, e.g., as a dietary or nutritional supplement or food additive for oral consumption.

As used herein, a "natural product" refers to a compound that exists in nature, i.e., is produced by a living source, as well as derivatives thereof. The natural products used in the present methods can either be isolated from a natural source, e.g., as an extract, or can be chemically synthesized (fully synthesized or semi-synthesized). The "natural products" used in the present methods and compositions can be either the natural products themselves (such as celastrol) or derivatives thereof (such as dihydrocelastrol, synthesized through the hydrogenation of celastrol). The combinations of natural products used in the present methods and compositions are novel and do not occur in nature.

Muscle "hypertrophy" refers to muscle growth that takes place via an increase in the size of skeletal muscle cells in response to an increase in load, without a concomitant increase in the number of muscle fibers. Muscle hypertrophy can be detected by virtue of, e.g., an increase in fiber cross-sectional area, in muscle mass, in muscle performance, or in other parameters.

The term "treating" or "treatment" refers to any one of the following: ameliorating one or more symptoms of a disease or condition; preventing the manifestation of such symptoms before they occur; slowing down or completely preventing the progression of the disease or condition (as may be evident by longer periods between reoccurrence episodes, slowing down or prevention of the deterioration of symptoms, etc.); enhancing the onset of a remission period; slowing down the irreversible damage caused in the progressive-chronic stage of the disease or condition (both in the primary and secondary stages); delaying the onset of said progressive stage; or any combination thereof. In the context of the present disclosure, the present methods and compositions can be used, e.g., to increase muscle growth, strength, mass, or performance for the treatment of conditions or diseases, e.g., to treat muscle atrophy resulting from conditions or diseases, such as post-surgery recovery, immobility, diabetes, cardiovascular disease, and cancer.

In some embodiments, the methods and compositions are used to enhance muscle growth, strength, mass, or function in healthy individuals, e.g., in the absence of muscle atrophy, e.g., in an individual desiring to increase their muscle mass for aesthetic, athletic, fitness-related, health-related, or other reasons.

The term "effective amount" or "effective dose" or "therapeutically effective amount" or "therapeutically effective dose" refers to an amount of a compound (e.g., a SIRT1 inhibitor) that is sufficient to bring about a beneficial or desired clinical or physiological effect. For example, in the present disclosure a therapeutically effective amount or dose of a compound or natural product could be any amount or dose that increases or enhances one or more aspects of muscle function, mass, hypertrophy, strength, performance, or other feature in a subject. An effective amount or dose may be based on factors individual to each subject, including, but not limited to, the subject's age, size, level of physical fitness, diet, genetic background, presence of any disease or condition, route of administration, the type or extent of any supplemental therapies used, etc. In some embodiments, an effective amount of a compound or natural product, as described herein, can be estimated initially from, e.g., cell culture or in vitro assays (e.g., by determining SIRT1 inhibition) or animal models (e.g., by assessing muscle growth, function, mass, strength, etc.).

The terms "subject" and "individual," and "patient" are used interchangeably herein to refer to a vertebrate, preferably a mammal, more preferably a human. Mammals include, but are not limited to, murines, rats, simians, humans, farm animals or livestock for human consumption such as pigs, cattle, and ovines, as well as sport animals and pets.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

3. Detailed Description of the Embodiments

The present disclosure is based on the surprising discovery that specific combinations of natural products can promote hypertrophy of skeletal muscle and thereby increase various features of muscles including mass, strength, endurance, fiber CSA (cross-sectional area), performance, and function. The products can be administered by any route, including orally, e.g., as a nutritional supplement or food additive. In some embodiments, the administration of the compounds leads to a decrease in SIRT1 levels or activity, and/or to an increase in the acetylation of SIRT1 substrates such as p53 or the ribosomal S6 protein kinase (S6K1).

In some embodiments, the hypertrophic muscles are subject to loading, e.g., through weight training or resistance training, that takes place in parallel to the administration of the natural products. While loading of skeletal muscle normally leads to hypertrophy and an increase in, e.g., muscle mass, fiber CSA, and strength even in the absence of the present compounds, the extent of hypertrophy and the increase in, e.g., muscle mass, fiber CSA, and strength is substantially greater in the presence of the present compounds than in their absence. In some embodiments, the increase in hypertrophy, muscle mass, strength, or other feature in the presence of the natural products and with loading is at least 10%, 20%, 30%, 40%, 50% or more greater than the increase seen with loading but in the absence of the natural products. In some embodiments, the loading takes place without aerobic activity. In some embodiments, the natural products are administered in parallel to muscle-growth-promoting amino acids or proteins, e.g., leucine, branched-chain amino acids, or proteins with high leucine content such as whey protein. Such amino acids or proteins can be formulated together with the natural products or separately, and can be administered at the same time as the products or according to an independent regimen. In some embodiments, the caloric intake of the subject is increased in parallel with the administration of the present compounds and the muscle loading.

Subjects

The subject can be any subject, e.g., human or other mammal, for whom an increase in muscle hypertrophy, growth, mass, strength, performance, or function would be desirable. In some embodiments, the subject is human. In some embodiments, the subject is an adult. In some embodiments, the subject is a child. In some embodiments, the subject is an adolescent. In some embodiments, the subject is female. In some embodiments, the subject is male.

In some embodiments, the subject has a disease or condition associated with a loss of muscle mass or function (e.g., muscle atrophy) such as diabetes, cardiovascular disease, immobility, cancer, cachexia, or post-surgery recovery, and the natural products are administered in order to restore or increase the mass, function, fiber CSA, or other feature of the atrophied muscle in the subject. In general, any disease or condition that involves a loss of skeletal muscle mass or function, or that could benefit in any way from an increase in the mass or function of one or more skeletal muscles, can be treated using the present methods and compositions.

In some embodiments, the subject does not have a disease or condition associated with a loss of muscle mass or function, and does not have atrophied muscle, but is instead desirous of increasing muscle mass or function for another reason, e.g., to increase strength, improve coordination, enhance athletic performance, increase bone density, improve metabolism, strengthen ligaments and tendons, reduce the risk of injury, or for aesthetic reasons.

In particular embodiments, the present compositions are administered in conjunction with loading of the skeletal muscles, e.g., loading of the skeletal muscles in the absence of aerobic activity. The loading can be performed, for example, through weight training (e.g., free weights), weight machines, resistance bands, or exercises using the subject's body weight for resistance. The loading can be continuous or episodic, high-load or low-load with, e.g., fewer or greater repetitions per set, respectively. The loading can be focused on one or a small number of muscles or more generally on muscles throughout the body.

Any skeletal muscle can be affected by the present methods and compositions, including the musculi pectoralis complex, latissimus dorsi, *teres* major and subscapularis, brachioradialis, biceps, *brachialis*, pronator quadratus, pronator *teres*, flexor carpi radialis, flexor carpi ulnaris, flexor digitorum superficialis, flexor digitorum *profundus*, flexor pollicis *brevis*, opponens pollicis, adductor pollicis, flexor pollicis *brevis*, iliopsoas, psoas, rectus abdominis, rectus femoris, gluteus maximus, gluteus medius, medial hamstrings, gastrocnemius, lateral hamstring, quadriceps mechanism, adductor longus, adductor *brevis*, adductor magnus, gastrocnemius medial, gastrocnemius lateral, soleus, tibialis posterior, tibialis anterior, flexor digitorum longus, flexor digitorum *brevis*, flexor hallucis longus, extensor hallucis longus, ocular muscles, pharyngeal muscles, sphincter muscles, hand muscles, arm muscles, foot muscles, leg muscles, chest muscles, stomach muscles, back muscles, buttock muscles, shoulder muscles, head and neck muscles, and the like.

In some embodiments, the compositions result in a decrease in SIRT1 activity in the muscles of the subject. In some embodiments, the compositions result in an increase in the acetylation of one or more ribosomal proteins in the subject. In some embodiments, the compositions do not substantially alter the body mass or the weight of the heart or liver of the subject.

Assessing SIRT1 Levels

Any of a number of methods can be used to assess the level or activity of SIRT1 in muscles, e.g., when assessing the efficacy of an inhibitor of SIRT1 or when assessing the level or activity of SIRT1 in a subject. For example, the level of SIRT1 can be assessed by examining the transcription of a gene encoding SIRT1 (e.g., the SIRT1 gene), by examining the levels of SIRT1 protein, by measuring SIRT1 enzyme activity, or indirectly by measuring, e.g., the acetylation of a SIRT1 substrate such as p53.

In some embodiments, the methods involve the measurement of SIRT1 enzyme activity, e.g., using standard methods such as incubating a candidate compound in the presence of SIRT1 and p53 in an appropriate reaction buffer (e.g., containing excess nicotinamide adenine dinucleotide) and monitoring deacetylation by a mobility shift assay based on charge differences before and after electrophoretic separation of product from fluorescently labeled substrate read, e.g., using a device such as a Caliper EZ Reader (see, e.g., Example 1).

In some embodiments, the methods involve the detection of SIRT1-encoding polynucleotide (e.g., mRNA) expression, which can be analyzed using routine techniques such as RT-PCR, Real-Time RT-PCR, semi-quantitative RT-PCR, quantitative polymerase chain reaction (qPCR), quantitative RT-PCR (qRT-PCR), multiplexed branched DNA (bDNA) assay, microarray hybridization, or sequence analysis (e.g., RNA sequencing ("RNA-Seq")). Methods of quantifying polynucleotide expression are described, e.g., in Fassbinder-Orth, *Integrative and Comparative Biology*, 2014, 54:396-406; Thellin et al., *Biotechnology Advances*, 2009, 27:323-333; and Zheng et al., *Clinical Chemistry*, 2006, 52:7 (doi: 10/1373/clinchem.2005.065078). In some embodiments, real-time or quantitative PCR or RT-PCR is used to measure the level of a polynucleotide (e.g., mRNA) in a biological sample. See, e.g., Nolan et al., *Nat. Protoc*, 2006, 1:1559-1582; Wong et al., *BioTechniques*, 2005, 39:75-75. Quantitative PCR and RT-PCR assays for measuring gene expression are also commercially available (e.g., TaqMan® Gene Expression Assays, ThermoFisher Scientific).

In some embodiments, the methods involve the detection of SIRT1 protein expression or stability, e.g., using routine techniques such as immunoassays, two-dimensional gel electrophoresis, and quantitative mass spectrometry that are known to those skilled in the art. Protein quantification techniques are generally described in "Strategies for Protein Quantitation," *Principles of Proteomics*, 2nd Edition, R. Twyman, ed., Garland Science, 2013. In some embodiments, protein expression or stability is detected by immunoassay, such as but not limited to enzyme immunoassays (ETA) such as enzyme multiplied immunoassay technique (EMIT), enzyme-linked immunosorbent assay (ELISA), IgM antibody capture ELISA (MAC ELISA), and microparticle enzyme immunoassay (META); capillary electrophoresis immunoassays (CEIA); radioimmunoassays (RIA); immunoradiometric assays (TRIVIA); immunofluorescence (IF); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis*, 18:2184-93 (1997); Bao, *J. Chromatogr. B. Biomed. Sci.*, 699:463-80 (1997)).

Any of a number of features of the muscle can be enhanced by the natural products, including the mass, strength, fiber cross-sectional area (CSA), protein content, fiber volume, muscle efficiency, performance, etc. Muscle growth and performance can be measured using any of a number of methods, e.g. imaging (e.g., X-rays, MM, CT, ultrasound), by molecular or cellular analysis in, e.g., a muscle biopsy taken from the subject biopsy, or by any functional test such as grip test, walk speed, muscle power test, resistance tests, treadmill, or other functional tests.

Compounds

The present disclosure is based upon the surprising discovery that specific combinations of natural products can promote hypertrophy in skeletal muscle, e.g., skeletal muscle undergoing loading. The herein-described combinations comprise one or more catechins, as well as celastrol or a derivative thereof. In some embodiments, the one or more catechins and the celastrol or derivative thereof inhibit SIRT1, e.g., lead to a decrease in the expression, stability, or activity of SIRT1, of at least 10%, 15%, 20%, 25%, 30%, 35%, 40%, 45%, 50%, 55%, 60%, 65%, 70%, 75%, 80%, 85%, 90%, or more relative to a control level, e.g., in the absence of the inhibitor, in vivo or in vitro. In one embodiment, the activity of SIRT1 is assessed in vitro using p53 as a substrate, e.g., by examining the acetylation of lysine 382, e.g., by assaying for a mobility shift resulting from SIRT1 deacetylase activity, e.g., as described in Example 1.

In some embodiments, the one or more catechins, and the celastrol or derivative thereof, lead to an increase in one or more properties of one or more muscles in the subject, e.g., of growth, mass, strength, performance, fiber volume, fiber cross-sectional area, by, e.g., at least 10%, 20%, 30%, 40%, 50%, 60%, 70%, 80%, 90% or more compared to a control level, e.g., the level in the absence of the one or more catechins and the celastrol or celastrol derivative.

In some embodiments, the one or more catechins included in the combination are epicatechins. In particular embodiments, the one or more epicatechins included in the combination are epicatechin and epigallocatechin-3-monogallate. The combinations can comprise any of a variety of amounts of each of the natural products. For example, the combinations can be formulated and administered such that the subject receives about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20 or more mg/kg/day of any of the compounds. In some embodiments, the combination is formulated and administered such that the subject receives about 0.7-1.3 mg/kg/day of epicatechin. In some embodiments, the combination is formulated and administered such that the subject receives about 0.7 mg/kg/day of epicatechin. In some embodiments, the combination is formulated and administered such that the subject receives about 6-20 mg/kg/day of epigallocatechin-3-monogallate. In some embodiments, the combination is formulated and administered such that the subject receives about 20 mg/kg/day of epigallocatechin-3-monogallate.

In some embodiments, the combination comprises celastrol or a celastrol derivative such as dihydrocelastrol. In some embodiments, the combination is formulated and administered such that the subject receives about 0.2-0.5 mg/kg/day of the celastrol or celastrol derivative. In some embodiments, the combination is formulated and administered such that the subject receives about 0.5 mg/kg/day of the celastrol or celastrol derivative. In some embodiments, the combination is formulated and administered such that the subject receives about 0.7-1.3 mg/kg/day of epicatechin, about 6-20 mg/kg/day of epigallocatechin-3-monogallate, and about 0.2-0.5 mg/kg/day of celastrol. In particular embodiments, the combination is formulated and administered such that the subject receives about 0.7 mg/kg/day of epicatechin, about 20 mg/kg/day of epigallocatechin-3-monogallate, and about 0.5 mg/kg/day of celastrol. In some embodiments, the combination is formulated (and/or administered) such that the relative weight ratio of the epicatechin, epigallocatechin-3-monogallate, and celastrol in the composition (and/or received by the subject, e.g., per administration or per day) is about 0.7:20:0.5, respectively (i.e., the composition could comprise, e.g., 0.7 mg epicatechin, 20 mg epigallocatechin-3-monogallate, and 0.5 mg celastrol, or any multiple or fraction of these amounts so long that the relative weight ratio of the three components remains about 0.7:20: 0.5). In some embodiments, the combination is formulated (and/or administered) such that the relative mole ratio of the epicatechin, epigallocatechin-3-monogallate, and celastrol in the composition (and/or received by the subject, e.g., per administration or per day) is about 1.6:43.6:1.1, respectively (i.e., the composition could comprise, e.g., 1.6 mmol epicatechin, 43.6 mmol epigallocatechin-3-monogallate, and 1.1 mmol celastrol, or any multiple or fraction of these amounts so long that the relative mole ratio of the three components remains about 1.6:43.6:1.1).

In some embodiments, celastrol or a celastrol derivative is administered alone or in combination with one or more additional compounds other than a catechin. In some embodiments, the celastrol or celastrol derivative, alone or in combination with the one or more non-catechin compounds, leads to a decrease in the expression, stability, or activity of SIRT1, of at least 10%, 15%, 20%, 25%, 30%, 35%, 40%, 45%, 50%, 55%, 60%, 65%, 70%, 75%, 80%, 85%, 90%, or more relative to a control level, e.g., in the absence of the celastrol, celastrol derivative, or celastrol-comprising combination, in vivo or in vitro. In some embodiments, the celastrol or celastrol derivative, alone on in combination with the one or more non-catechin compounds, leads to an increase in one or more properties of one or more muscles in the subject, e.g., growth, mass, strength, performance, fiber volume, fiber cross-sectional area, by, e.g., at least 10%, 20%, 30%, 40%, 50%, 60%, 70%, 80%, 90% or more compared to a control level, e.g., the level in the absence of the celastrol, celastrol derivative, or celastrol-comprising combination.

When administered alone or in a combination with one or more additional non-catechin compounds, the celastrol or celastrol derivative can be formulated and administered at any of a range of amounts, e.g., such that the subject receives about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20 or more mg/kg/day of any of the compounds. In some embodiments, the celastrol or celastrol derivative is formulated and administered such that the subject receives about 0.2-0.5 mg/kg/day of the celastrol or celastrol derivative. In some embodiments, the celastrol or celastrol derivative is formulated and administered such that the subject receives about 0.5 mg/kg/day of the celastrol or celastrol derivative.

The herein-described natural products can be obtained from a variety of sources, including from natural sources, through chemical synthesis, and from chemical vendors. For example, epicatechin can be isolated, e.g., from green tea, grapes, or obtained from, e.g., Aurora fine chemicals, Sigma-Aldrich, Combi-Blocks, ChemShuttle, and others.

Epigallocatechin monogallate can be isolated, e.g., from green tea or black tea, or obtained from, e.g., Sigma-Aldrich, Combi-Blocks, King Scientific, and others. Celastrol can be isolated, e.g., from the root extracts of *Tripterygium* wildordii and *Celastrus regelii*, or obtained from, e.g., *Aurum* Pharmatech, Achemtek, ChemShuttle, VWR, and others. Dihydrocelastrol can be synthesized, e.g., through the hydrogenation of celastrol, or can be obtained, e.g., from AbovChem, Achemtek, *Aurum* Pharmatech, Sigma-Aldrich, and others.

Formulation and Administration

The herein-disclosed compounds can be formulated and administered in any of a number of ways. In some embodiments, the compounds are formulated as a pharmaceutical composition, i.e. comprising a pharmaceutically acceptable carrier. In certain aspects, pharmaceutically acceptable carriers are determined in part by the particular composition being administered, as well as by the particular method used to administer the composition. Accordingly, there is a wide variety of suitable formulations of pharmaceutical compositions of the present compounds (see, e.g., *REMINGTON'S PHARMACEUTICAL SCIENCES*, 18TH ED., Mack Publishing Co., Easton, Pa. (1990)).

As used herein, "pharmaceutically acceptable carrier" comprises any of standard pharmaceutically accepted carriers known to those of ordinary skill in the art in formulating pharmaceutical compositions. Thus, the compounds, by themselves, such as being present as pharmaceutically acceptable salts, or as conjugates, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or the like, or as solid formulations in appropriate excipients.

The pharmaceutical compositions will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, solutes that render the formulation isotonic, hypotonic or weakly hypertonic with the blood of a recipient, suspending agents, thickening agents, preservatives, flavoring agents, sweetening agents, and coloring compounds as appropriate.

The herein-described pharmaceutical compositions are administered in a manner compatible with the dosage formulation, and in such amount as will be therapeutically effective. The quantity to be administered depends on a variety of factors including, e.g., the age, body weight, physical activity, and diet of the individual, any conditions or diseases to be treated, and the stage or severity of any potential conditions or diseases. In certain embodiments, the size of the dose may also be determined by the existence, nature, and extent of any adverse side effects that accompany the administration of a therapeutic agent(s) in a particular individual.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the presence and severity of any particular condition, and any other potential therapies that are being administered.

In certain embodiments, the dose of the compound may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for humans and other mammals, each unit containing a predetermined quantity of a therapeutic agent calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times, the amount of the therapeutic compound.

Methods for preparing such dosage forms are known to those skilled in the art (see, e.g., *REMINGTON'S PHARMACEUTICAL SCIENCES*, supra). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., *REMINGTON'S PHARMACEUTICAL SCIENCES*, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

In particular embodiments, the compounds are formulated for oral, buccal, or sublingual administration. For example, the therapeutically effective dose can be in the form of tablets, capsules, pills, pellets, gelcaps, gummies, emulsions, suspensions, solutions, syrups, elixirs, pastes, gels, granules, gums, liquids, powders, rapidly-dissolving tablets, effervescent formulations, sachets, semi-solids, sprays, lozenges, powders, tinctures, and sustained-release formulations. Suitable excipients for administration include pharmaceutical grades of mannitol, lactose, starch, magnesium stearate, sodium saccharine, talcum, cellulose, glucose, gelatin, sucrose, magnesium carbonate, and the like.

In particular embodiments, the natural products are formulated as a nutritional supplement or a food additive, e.g., as a pill, tablet, capsule, liquid, powder, energy bar, protein bar, gummy, chocolate, candy, mint, etc., optionally comprising other elements such as sweeteners, flavoring agents, coloring agents, protein, amino acids such as leucine or other branched-chain amino acids, etc.

In addition to the herein-described natural products, compositions for oral administration may optionally contain, e.g., carrier materials such as corn starch, acacia, gelatin, malt, tragacanth, microcrystalline cellulose, kaolin, dicalcium phosphate, calcium carbonate, sodium chloride, alginic acid, lactose, glucose, or sucrose; disintegrators such as microcrystalline cellulose or alginic acid; binders such as acacia, methylcellulose, ethyl cellulose, sodium carboxymethylcellulose, polyvinylpyrrolidone, or hydroxypropyl methylcellulose; and/or lubricants such as magnesium stearates, stearic acid, silicone fluid, talc, oils, waxes, colloidal silica, etc.

The natural products can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In some embodiments, additional compounds or medications can be co-administered to the subject. Such compounds or medications can be co-administered for the purpose of alleviating signs or symptoms of the disease being treated, reducing side effects caused by induction of the immune response, etc. In some embodiments, for example, the natural products are administered together with a muscle-growth-promoting amino acid such as leucine or a branched-chain amino acid, or with leucine-rich protein, and/or any other compound aiming to enhance muscle mass, strength, or function, e.g., another SIRT1 inhibitor.

The present compounds can be administered locally in the subject or systemically. In some embodiments, the compounds can be administered, for example, intraperitoneally, intramuscularly, intra-arterially, orally, intravenously, intracranially, intrathecally, intraspinally, intralesionally, intranasally, subcutaneously, intracerebroventricularly, topically, transdermally, sublingually, buccally, and/or by inhalation. In particular embodiments, the compounds are administered orally, e.g., as a food additive.

In some embodiments, the compounds are administered to the subject once. In other instances, the compounds are administered at one time point, and administered again at a second time point. In yet other instances, the compounds are administered to the subject repeatedly (e.g., once or twice daily) as intermittent doses over a limited period of time (e.g., 2 days, 3 days, 4 days, 5 days, 6 days, a week, 2 weeks, 3 weeks, 4 weeks, a month, or more). In some cases, the time between administrations of the compounds is about 1 day, 2 days, 3 days, 4 days, 5 days, 6 days, a week, 2 weeks, 3 weeks, 4 weeks, a month, or more. In other embodiments, the compounds are administered continuously or chronically over a desired period of time. For instance, the compounds can be administered such that the amounts or levels of the compounds are substantially constant over a selected time period. In some embodiments, the compounds are administered over a prolonged period of time, e.g., several months or longer, e.g., in parallel with a weight training program of indeterminate duration.

Administration of the compounds to a subject can be accomplished by methods generally used in the art. The quantity of the compounds introduced will take into consideration factors such as sex, age, weight, the presence or absence of a disease or condition, the presence or absence of muscle atrophy, the specific goals and motivations of the subject for increasing muscle mass, strength, or function, and the quantity needed to produce the desired result. Generally, for administering the compounds for therapeutic or other purposes, the compounds are given at an "effective dose" or "therapeutically effective dose". By "effective amount" or "effective dose" is an amount sufficient to produce the desired physiological effect or amount capable of achieving the desired result, including for treating a condition or disease, e.g., reducing or eliminating one or more symptoms or manifestations of the condition or disease, as well as for improving muscle mass in the absence of a disease or condition.

Any number of muscles of the body may undergo hypertrophy due to the presence of the herein-described compounds, such as, for example, the biceps muscle; the triceps muscle; the brachioradialus muscle; the *brachialis* muscle (*brachialis* anticus); the superficial compartment wrist flexors; the deltoid muscle; the biceps femoris, the gracilis, the semitendinosus and the semimembranosus muscles of the hamstrings; the rectus femoris, vastus lateralis, vastus *medialis* and vastus *intermedius* muscles of the quadriceps; the gastrocnemius (lateral and medial), tibialis anterior, and the soleus muscles of the calves; the pectoralis major and the pectoralis minor muscles of the chest; the latissimus dorsi muscle of the upper back; the rhomboids (major and minor); the trapezius muscles that span the neck, shoulders and back; the rectus abdominis muscles of the abdomen; the gluteus maximus, gluteus medius and gluteus minimus muscles of the buttocks; muscles of the hand; sphincter muscles; ocular muscles; and pharyngeal muscles.

4. Kits

Other embodiments of the compositions described herein are kits comprising the herein-described compounds. The kit typically contains containers, which may be formed from a variety of materials such as glass or plastic, and can include for example, bottles, vials, syringes, and test tubes. A label typically accompanies the kit, and includes any writing or recorded material, which may be electronic or computer readable form providing instructions or other information for use of the kit contents.

In some embodiments, the kit comprises one or more reagents for the promotion of muscle growth or hypertrophy. In some embodiments, the kit comprises one or more catechins, and celastrol or a derivative thereof. In some embodiments, the kit comprises two catechins, and celastrol or a derivative thereof. In some embodiments, the two catechins are epicatechins. In some embodiments, the epicatechins are epicatechin-3-monogallate and epigallocatechin. In some embodiments, the kit further comprises one or more additional agents, e.g., one or more muscle-growth-promoting amino acids or proteins, e.g., leucine or a branched-chain amino acid, or a leucine-rich protein such as whey protein.

In some embodiments, the kits can further comprise instructional materials containing directions (i.e., protocols) for the practice of the present methods (e.g., instructions for using the kit for enhancing mass, strength, or function in atrophied or non-atrophied muscle). While the instructional materials typically comprise written or printed materials they are not limited to such. Any medium capable of storing such instructions and communicating them to an end user is contemplated by this disclosure. Such media include, but are not limited to electronic storage media (e.g., magnetic discs, tapes, cartridges, chips), optical media (e.g., CD ROM), and the like. Such media may include addresses to internet sites that provide such instructional materials.

5. Examples

Example 1. Increasing Muscle Hypertrophy with a Natural Product SIRT1 Inhibitor Introduction To determine whether SIRT1 inhibited muscle growth, our group previously removed the gastrocnemius and soleus muscles in wild type and muscle-specific SIRT1 knockout mice (mKO) and determined the compensatory growth in the plantaris (PLN) muscle. In SIRT1 mKO mice, there was a 113% greater increase in muscle mass over the 2 weeks of overload, when compared with wild type (WT) mice. Further, in mice overexpressing SIRT1 there was a small, but significant, impairment of muscle growth compared to WT mice. These data support the hypothesis that SIRT1 inhibits overload-induced muscle growth.

The goal of the current work was two-fold: first, we sought to identify natural products that could inhibit SIRT1; and second, we sought to determine whether these natural products could augment muscle hypertrophy when combined in the optimal manner. Overall, our hypothesis was that we could discover a novel nutritional supplement that could increase the effect of overload on muscle fiber cross-sectional area.

Materials and Methods
SIRT1 Inhibitor Screen

The NatProd Collection library (MicroSource Discovery Systems, Inc. Gaylordsville, Conn.) in ten source plates was screened at two doses (50 µM and 5 µM final in the reaction mixture, duplicate for each dose). The inhibitory activity of the compounds was assessed against 2 ng/µl purified human SIRT1 using 3 µM p53 as a substrate. The assay was a mobility shift assay based on charge differences before and after electrophoretic separation of product from fluorescently labeled substrate read using a Caliper EZ Reader (Perkin Elmer, Boston, Mass.). All reactions took place in the presence of excess nicotinamide adenine dinucleotide and the known SIRT1 inhibitor suramin was used as a control.

Box-Behnken Model Generation

Three of the inhibitors identified in the natural product screen were selected based on their previous use in humans and complementary chemical structures. These inhibitors were then used to create an incomplete multifactorial design Box-Behnken model using Design-Expert® software. The three-factor design with one central point required 13 animals. Five more animals received the central dose of all three natural products to determine the biological variability.

Synergist Ablation

All animal procedures were approved by the Institutional Animal Care and Use Committee at the University of California, Davis. Eighteen rats were used for both the DOE and validation experiments. The animals were anesthetized using 2.5% isoflurane, shaved and prepared for aseptic surgery. The whole soleus and bottom half of the gastrocnemius were removed at the Achilles tendon, leaving the plantaris (PLN) intact. The overlying fascia and skin were sutured shut, and the animals were moved to a temperature regulated area for recovery. The left leg served as a contralateral control. Animals were monitored daily to ensure they returned to normal activity and did not suffer any stress from the procedure. Animals were gavaged in accordance to their respective treatment groups daily just prior to lights out.

Muscle Collection

Following the 14th day of treatment, animals were anesthetized, and the overloaded and contralateral PLN muscles, hearts, and livers were collected. Upon removal, PLN muscles were trimmed conservatively, weighed and then pinned at resting length on cork, snap-frozen in liquid nitrogen cooled isopentane and stored at $-80°$ C.

Histology

PLN muscles were blocked in a cryostat on corks using OTC, and 10 µm sections were mounted onto slides for CSA quantification. Slides were prepped for histological analysis by being blocked in 5% normal goat serum (NGS) in PBST w/1% tween, and incubated in primary antibodies for type I, IIa, IIb fibers, and/or laminin overnight at 4° C. The next day, slides were washed with PBST w/0.1% Tween and incubated in HRP-conjugated secondary antibodies for 60 minutes, washed again and mounted using Prolong Gold (no Dapi). Four random images were taken of each respective muscle section for CSA quantification using Fiji.

Validation Experiment

Following synergist ablation, animals were randomly assigned to one of four treatment groups, control (n=3), Least (n=5), Moderate (n=5), and Optimal (n=5). The control group received phosphate buffered saline (PBS), whereas the least, moderate, and optimal groups received different combinations and concentrations of the 3 SIRT1 inhibitors as a single cocktail dissolved in PBS. All treatments were administered via oral gavage just prior to lights out for 14 days.

mRNA Isolation, Reverse Transcription and qPCR

Following blocking, PLN muscles were powdered using a hammer and pestle. Total RNA was extracted from powdered muscle tissue using RNAzol in accordance with the manufacturer's protocol. RNA was quantified using Biotek Epoch Microplate Reader via absorbance (Biotek, Winooski, Vt.). One and a half micrograms of total RNA were converted into cDNA using MultiScribe Reverse Transcriptase and oligo (DT) primers. cDNA was diluted 1:10 before qPCR. qPCR was performed using CFX384 Touch Real-Time PCR Detection System (Bio-Rad, Hercules, Calif.), along with Quantified Mastermix and Bio-Rad Sybr Green Mix solution and Bio-Rad 384 well PCR plates. PCR reactions were performed in accordance with the manufacturer's instructions with the following primers: rITS-1 (fwd-TCCGTTTTCTCGCTCTTCCC-(SEQ ID NO: 1); rev-CCGGAGAGATCACGTACCAC-(SEQ ID NO: 2)), r5E1TS (fwd-ACGCACGCCTTCCCAGAGG- (SEQ ID NO: 3); rev-CGCGTCTCGCCTGGTCTCTTG-(SEQ ID NO: 4)). Gene expression was calculated using a delta delta threshold cycle method (Livak and Schmittgen, 2001) and GAPDH was used as the housekeeping gene.

Tissue Homogenization and Western Blotting

Two scoops of powder were incubated in 250 μL of sucrose lysis buffer (1 M Tris, pH 7.5, 1 M sucrose, 1 mM EDTA, 1 mM EGTA, 1% Triton X-100, and protease inhibitor complex). The solution was set on a shaker for 60 minutes at 4° C., spun down at 8,000 g for 10 minutes, supernatants were transferred to new Eppendorf tubes and protein concentrations were then determined using a DC protein assay (Bio-Rad, Hercules, Calif.). 750 μg of protein was diluted in 4X Laemmli sample buffer (LSB) and boiled for 5 minutes. 10 μL of protein sample was loaded onto a Criterion TGX Stain-Free Precast Gel and run for 45 minutes at a constant voltage of 200V. Proteins were then transferred to an Immobilon-P PVDF membrane, after it was activated in methanol and normalized in transfer buffer at a constant voltage of 100V for 60 minutes. Membranes were blocked in 1% Fish Skin Gelatin (FSG) in TBST (Tris-buffered saline w/0.1% Tween) and incubated overnight at 4° C. with the appropriate primary antibody diluted in either TBST or FSG at 1:1,000. The next day, membranes were washed three times with TBST for 5 minutes, and successively incubated at room temperature with peroxidase-conjugated secondary antibodies in a 0.5% Nonfat Milk TBST solution at 1:5,000. Bound antibodies were detected using a chemiluminescence HRP substrate detection solution (Millipore, Watford, UK). Imaging and band quantification were determined using a BioRad.

Immunoprecipitations

Muscle powder was homogenized and protein quantified as above and 500 μg protein was placed into a tube containing 25 μL of antibody loaded Protein G-Dyna beads were aliquoted into an Eppendorf tube and prepped for immunoprecipitation using the instructed protocol (Thermo Scientific, Protein G-Dyna Beads). Antibodies for pulldown were used at a concentration of 1:100, and the final solution was submerged in a 30 μL of 1X LSB, boiled for 5 minutes and stored at −80° C. 6 μL of sample was loaded per well onto a Criterion TGX Stain-Free Precast Gel and carried forward with the western blotting protocol above.

Antibodies

Primary antibodies for western blotting and immunoprecipitation were diluted to a concentration of 1:1000. Antibodies were from Cell Signaling Technology (Danvers, Mass., United States)—total eEF2 (CS-23325), p-53 (CS-25245), phospho-eEF2 (CS-23315), SIRT1 (CS-947S), Ac-Lys (CS9441S), phospho-S6 (CS-5364S), Ac-p53 (CS-252S), P-AKT (Ser473) (CS-40605), Cytochrome-C(CS-42805); Santa Cruz Biotechnology (Santa Cruz, Calif., United States)—rps6 (SC-13007), rpL13a (SC-390131), Dystrophin (SC-465954); Abcam (Cambridge, UK)— Total OxPhos (ab110413); and Millipore-puromycin (MABE343).

Statistics

All data were analyzed using two-way ANOVA using GraphPad Prism software (GraphPad Software, Inc., La Jolla, Calif.). Tukey's post hoc analysis was used to determine differences when interactions existed. Statistical significance was set at $p<0.05$. All data are presented as mean±standard error mean (SEM).

Results

SIRT1 Inhibitor Screen

The high-throughput screen of 800 natural products identified 45 compounds that inhibited SIRT1 >65% at a concentration of 50 μM. Of these, many showed a dose-dependent effect on SIRT1, with 35 compounds showing at least 20% inhibition at 5 μM. Of the 35 inhibitors identified, 3 were already used extensively in human foods (Table 1) and came from 3 distinct chemical classes (one each quinone-methide, polyphenol, and flavonoid). These compounds (Celastrol, Epigallocatechin-3-Monogallate, and Epicatechin) were selected for further study with the goal of improving muscle hypertrophy in mammals.

DOE Model Generation

Figure 1A:
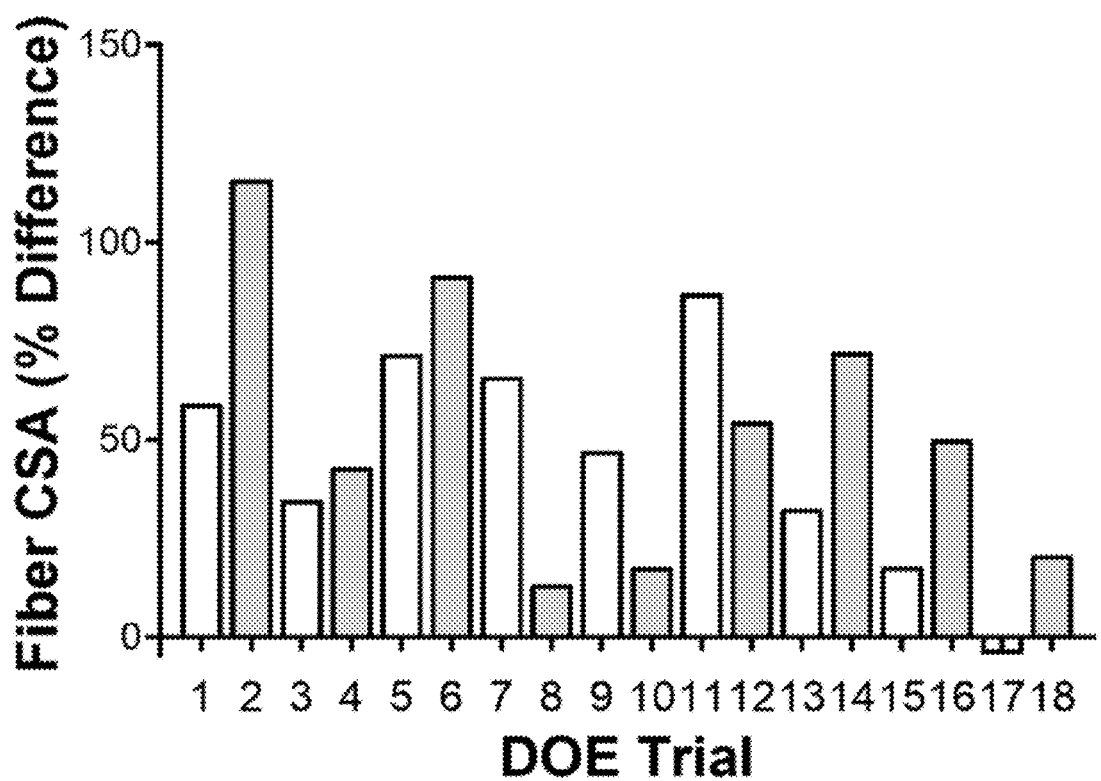
Figure 1B:
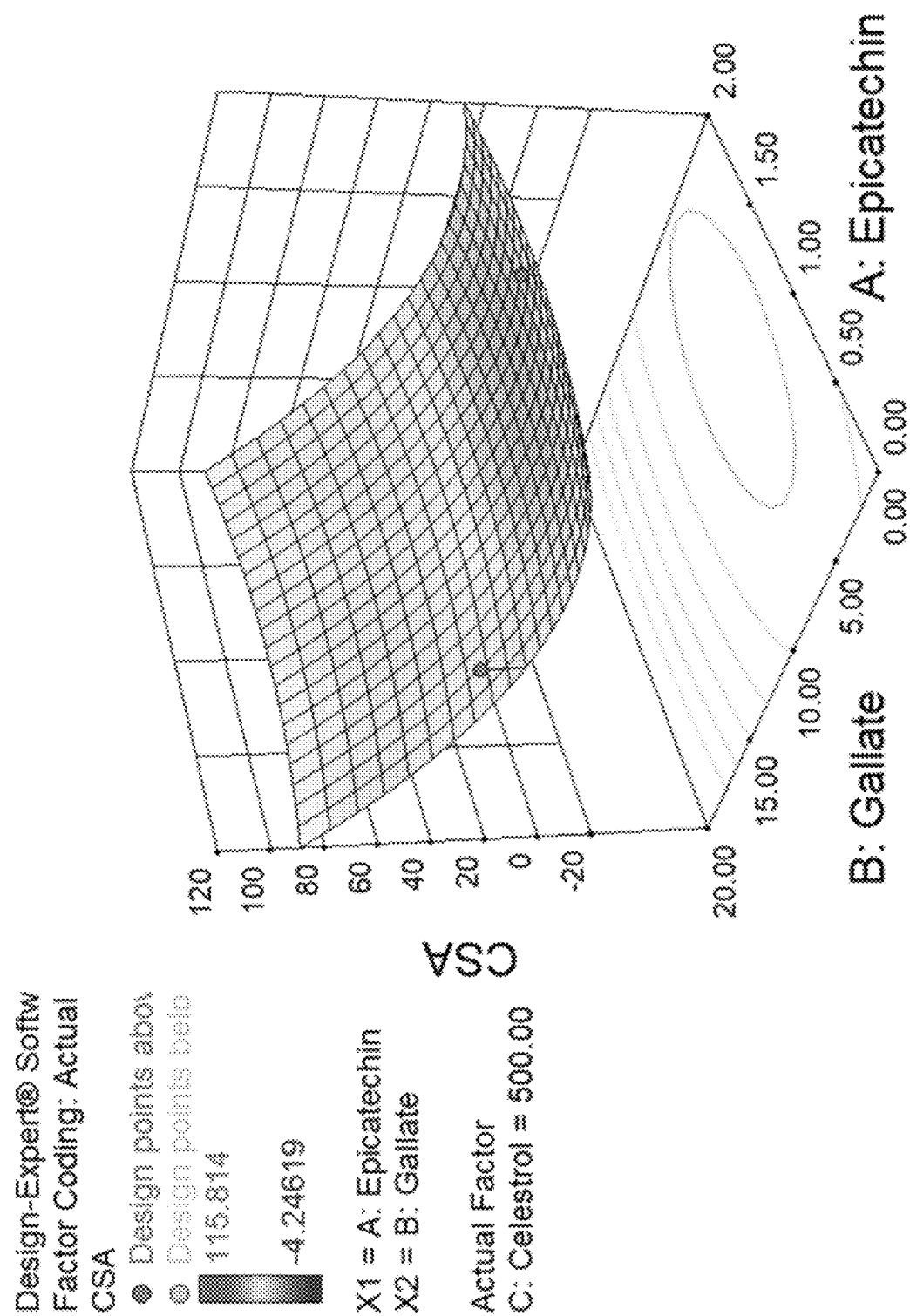

The three compounds identified above were entered into a Box-Behnken incomplete factorial design to quickly assess any interactions between the different products. Thirteen rats received different combinations of the three products (ranging from 0-2 mg/kg/day epicatechin; 0-10 mg/kg/day epigallocatechin-3-gallate; and 0-500 μg/kg/day celastrol), while five controls received the middle amount of each product to determine biological variability. Fourteen days of overload resulted in changes in muscle fiber cross-sectional area that ranged from −4.25% to 115.8% depending on the treatment (FIG. 1), with the controls averaging 66.8±6.98%. From these data, response surface plots indicated that the epigallocatechin-3-gallate could modulate the effect of the other two products and a model predicting the optimal combination and concentration of each product was produced (FIG. 1B).

Model Validation

Figure 2A:
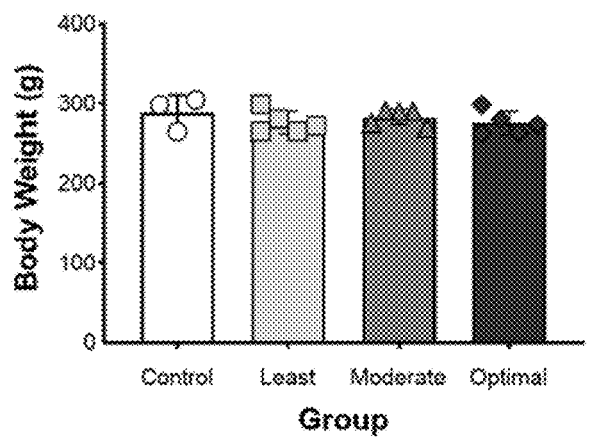
FIGS. 2A-2H. Validation of the Box-Behnken model of the relationship between natural products and muscle fiber cross-sectional area.
Figure 2B:
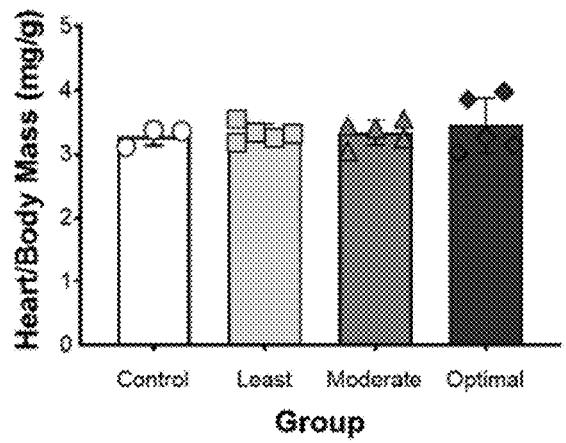
Figure 2C:
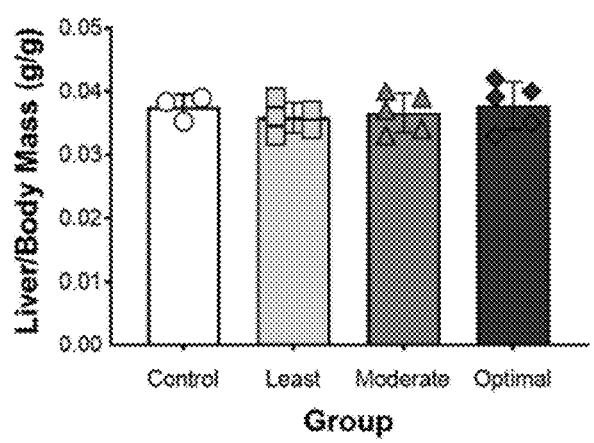
Figure 2D:
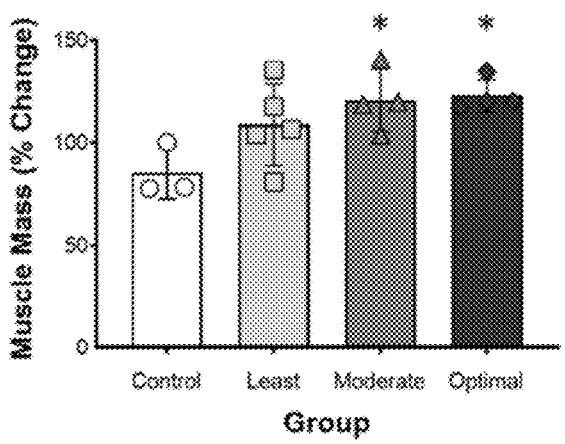
Figure 2E:
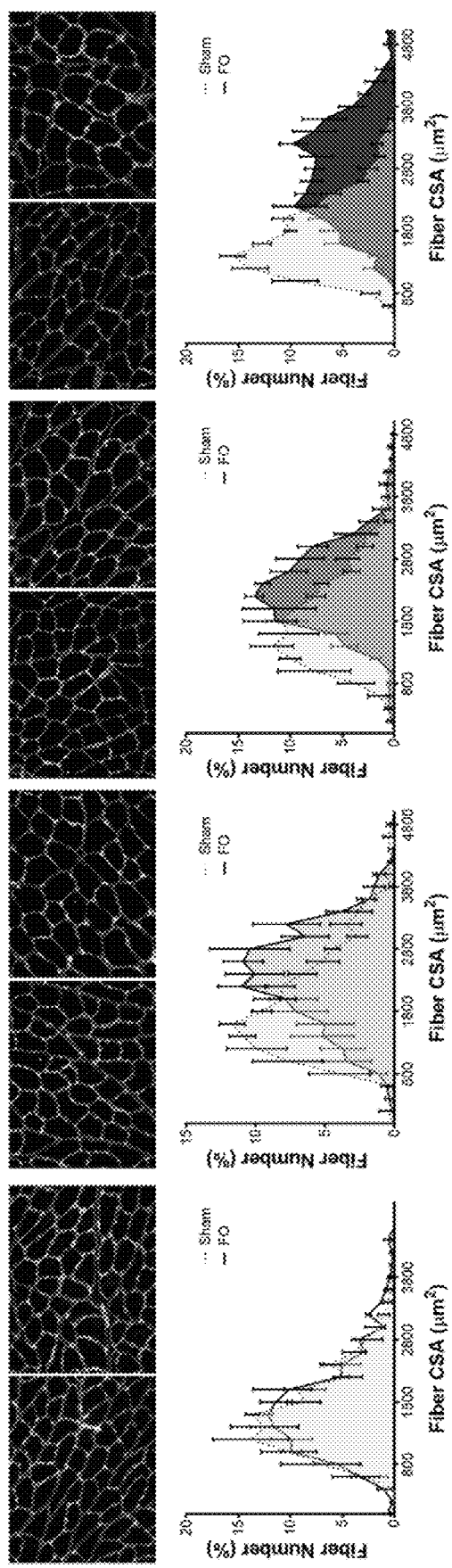
Figures 2F, 2G:
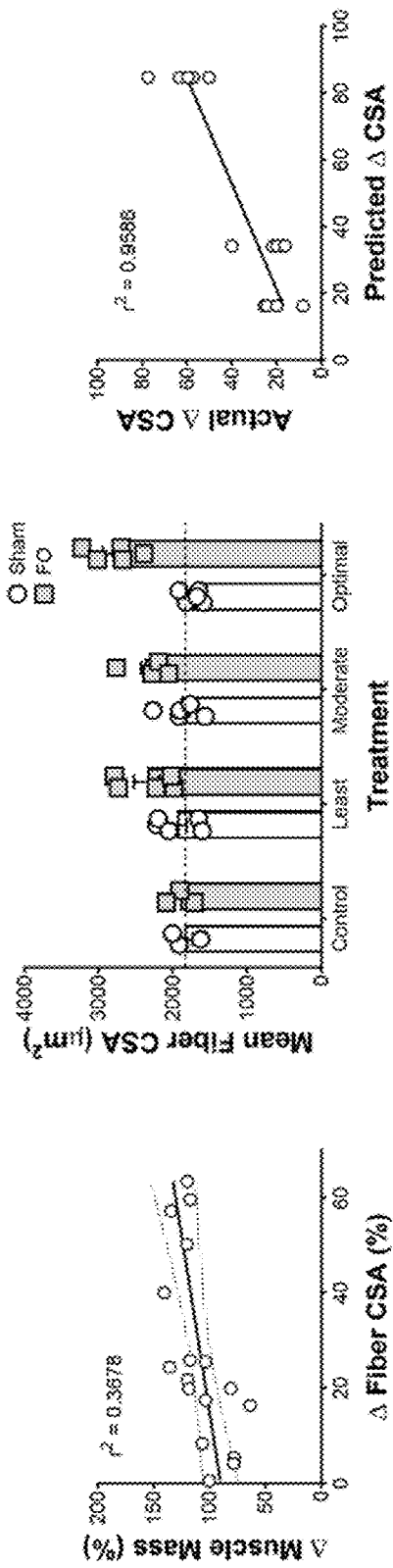
Figure 2H:
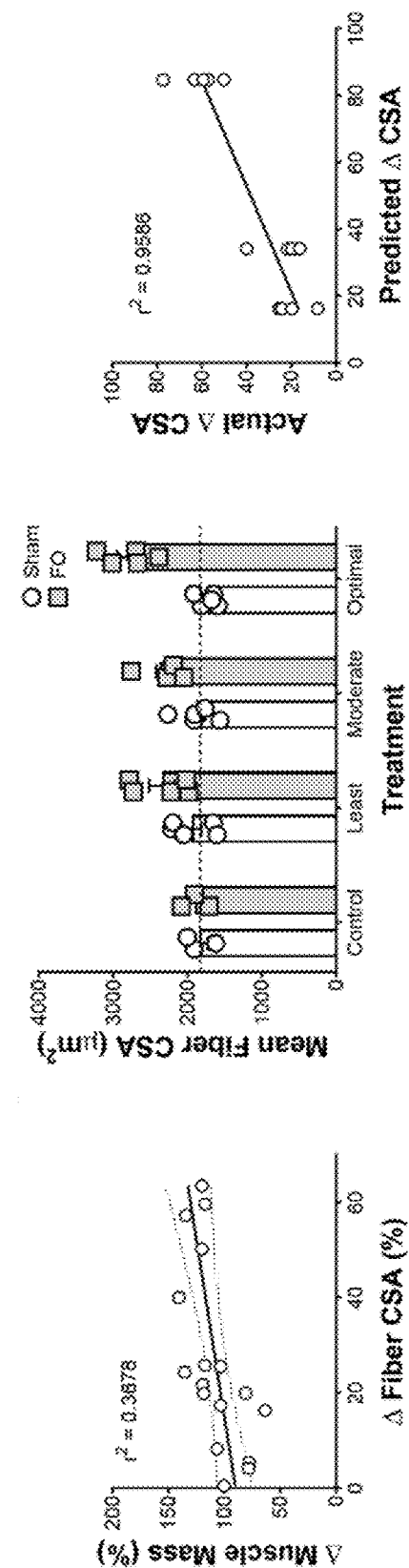
Figure 3A:
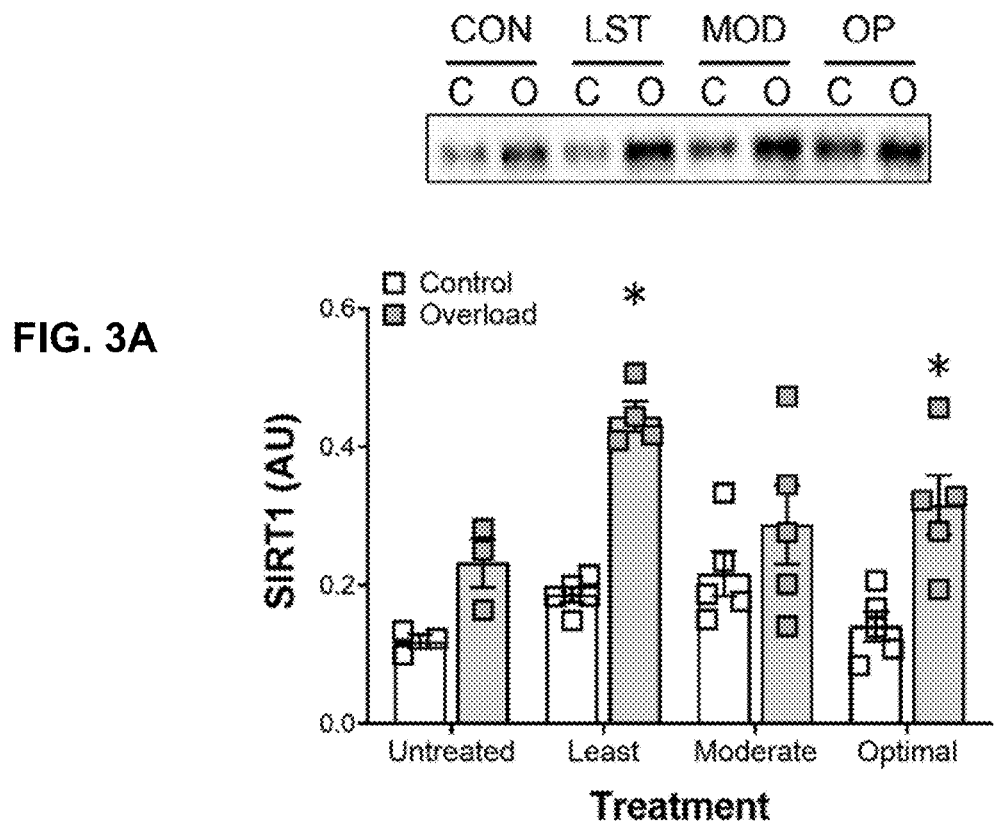
FIGS. 3A-3C. SIRT1 levels and acetylation with overload and natural product treatment.
Figure 3B:
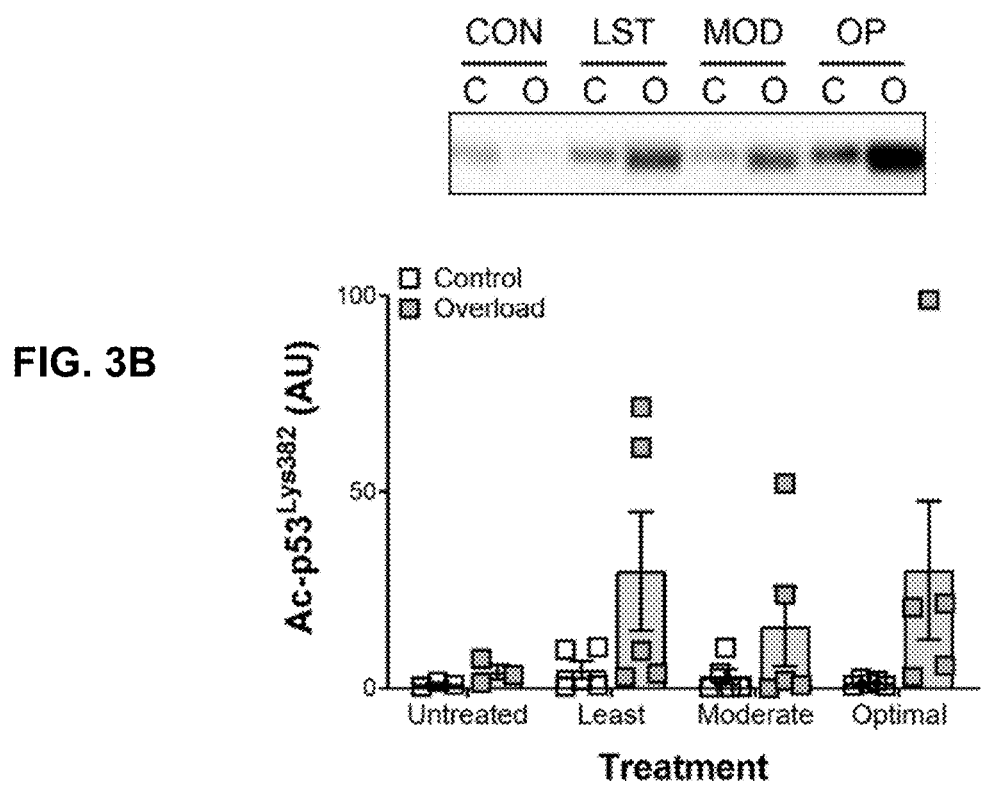
Figure 3C:
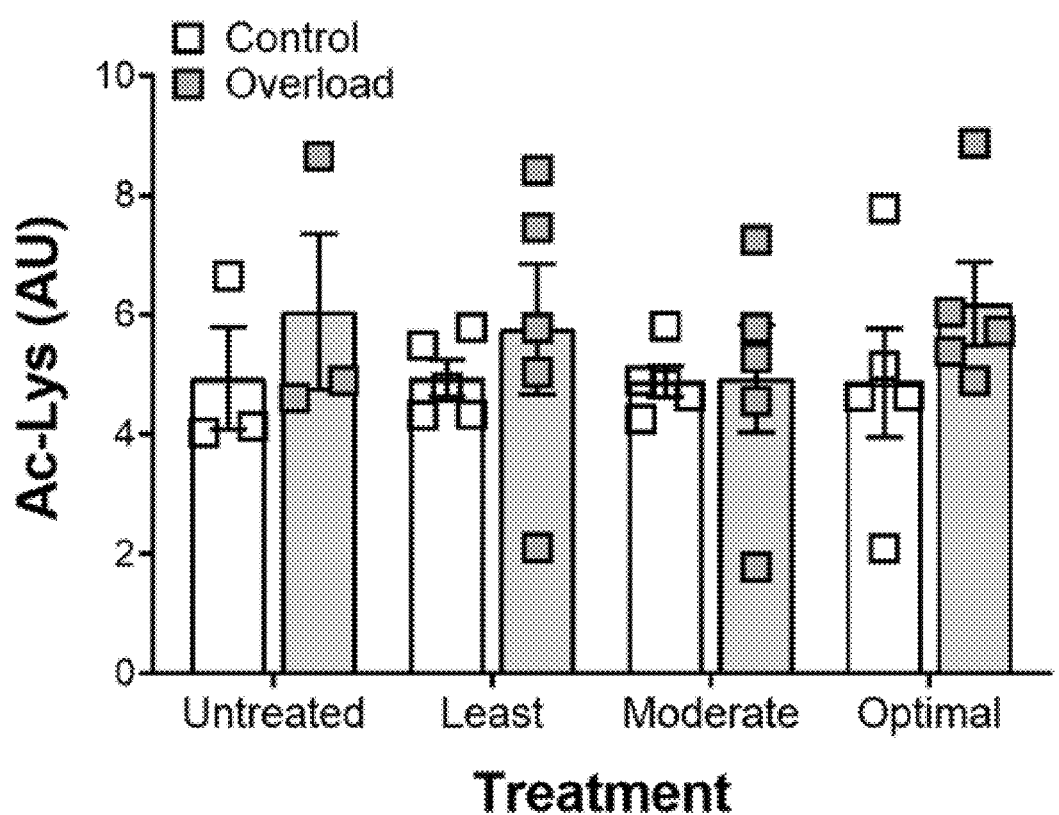

To validate the model, an independent group of rats underwent synergist ablation and then was gavaged daily with either a saline control or the predicted optimal, least effective, or a combination of the three products predicted to produce an increase in fiber CSA between the other two groups. The dose of each product for each group is outlined in Table 2. Following 14 days of overload and treatment, the animals were sacrificed, and body, heart, liver and muscle weights were determined (FIG. 2). There were no statistical differences between the untreated and treated groups for body, heart, or liver mass, suggesting that the treatment did not result in any acute toxicity. Both the moderate and optimal groups showed a significant increase in muscle mass relative to the control treated rats. Analysis of muscle fiber CSA demonstrated that the control legs showed similar distribution of fiber CSA regardless of treatment. There was a right shift in fiber CSA with overload that was greatest in the optimal group. The mean fiber CSA of the SHAM legs for all groups were 1847±114.6, 1945±132.5, 1883±114.6, and 1730±60.0 μm$^2$ for the control, least, moderate, and optimal groups, respectively, whereas the overloaded legs showed averages of 1901±108.3, 2348.1±172.8, 2306.5±119.7, and 2800±145.9 μm$^2$, for the respective groups (FIG. 2G). To test the predictive power of the Box-Behnken model, the predicted change in fiber CSA was plotted against the measured value for each of the groups. The resulting line had an r$^2$ value of 0.9586 validating the ability of the model to predict changes in muscle hypertrophy (FIG. 2H).

SIRT1 Levels and Activity

Since the treatment was meant to inhibit SIRT1, the levels of SIRT1 and a gauge of its enzyme activity (p53 acetylation) were determined (FIG. 2). As overserved previously, the levels of SIRT1 increased significantly following overload in the control group (~2-fold) and SIRT1 levels were even higher in both the control and overloaded limbs following treatment with the SIRT1 inhibitors. As a measure of SIRT1 activity, we determined the levels of acetylation of p53 at lysine 382. As has been reported for other SIRT1 inhibitors (16), overload together with treatment with the natural product cocktails increased p53 acetylation at this residue; however, there was no difference in p53 acetylation with the different doses. Lastly, to determine whether the natural product cocktail altered global protein acetylation, total acetylated proteins were measured and there was no statistical difference in total acetylated proteins with any of the treatments at the two-week time point.

Protein Synthetic Response

Figure 4D:
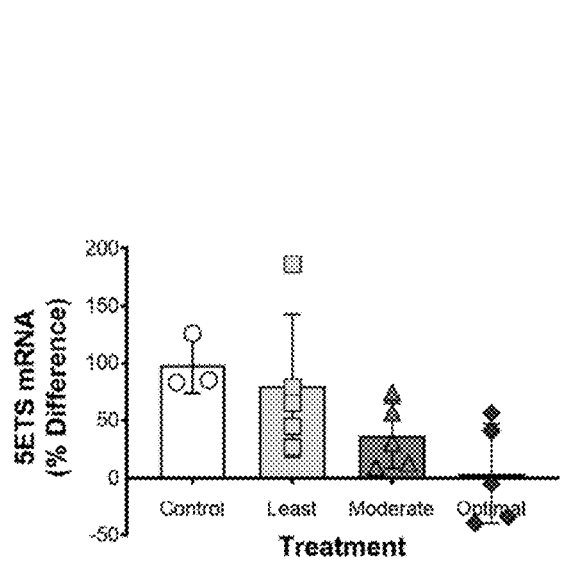
Figure 4E:
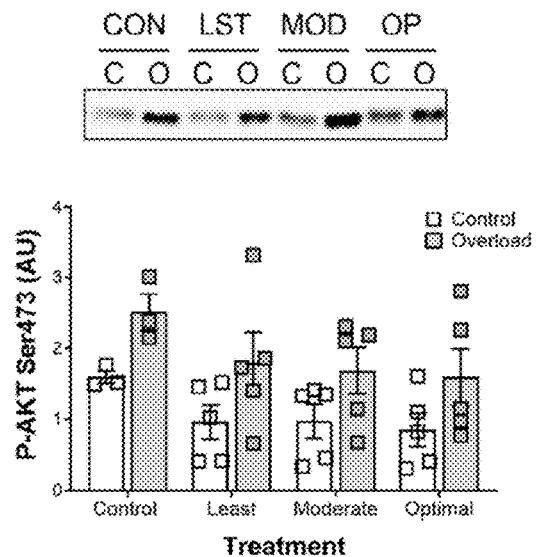
Figure 4F:
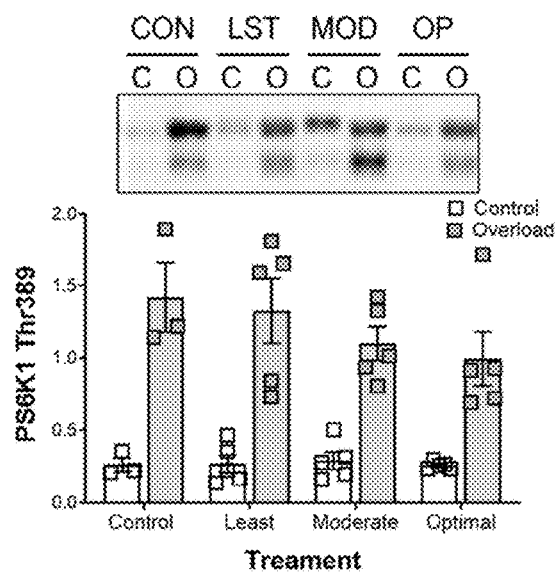
Figure 4G:
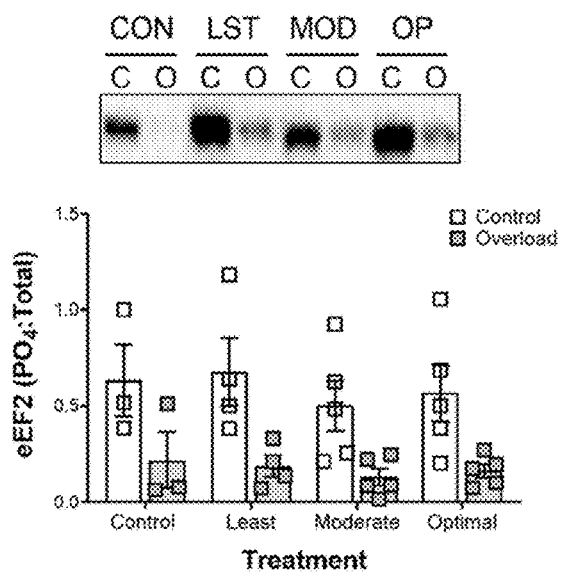

To begin to understand the mechanism through which the natural products were increasing muscle fiber CSA, the rate of protein synthesis was determined by SuNSeT. Even though there was a trend for baseline protein synthesis to increase with the natural product cocktail, the increase in protein synthesis with overload was similar across all treatment groups (FIG. 4A). Since ribosome mass is thought to control protein synthesis in extreme states, such as during overload, we next determined total RNA and the rate of ribosome biogenesis. Contrary to our hypothesis, total RNA tended to decrease from control to optimal treatment. Further, when the rate of ribosomal RNA synthesis was determined by measuring the expression of the internal transcribed spacer 1 (ITS1) and 5' external transcribed spacer (5'ETS), the expression of these markers of ribosomal biogenesis decreased from control, to least, to moderate, to optimal where the 5'ETS value was significantly lower than the control treated muscles (FIGS. 4C-4D). To determine whether the increased growth in the natural product groups was the result of greater Akt-mTORC1 signaling, the phosphorylation of Akt, S6K1, and eEF2 were determined. There was a tendency for Akt phosphorylation to increase with overload and decrease in the natural products (FIG. 4E); however, neither of these effects reached significance. As reported previously, S6K1 phosphorylation was higher in the overloaded leg (FIG. 4F). Contrary to expectation, there was a trend for overload-induced S6K1 phosphorylation to decrease from control towards the optimal natural product combination; however, the activity of S6K1 (determined through eEF2 phosphorylation) was no different in any of the overloaded groups (FIG. 4G).

Markers of Protein Turnover/Degradation

Figure 5A:
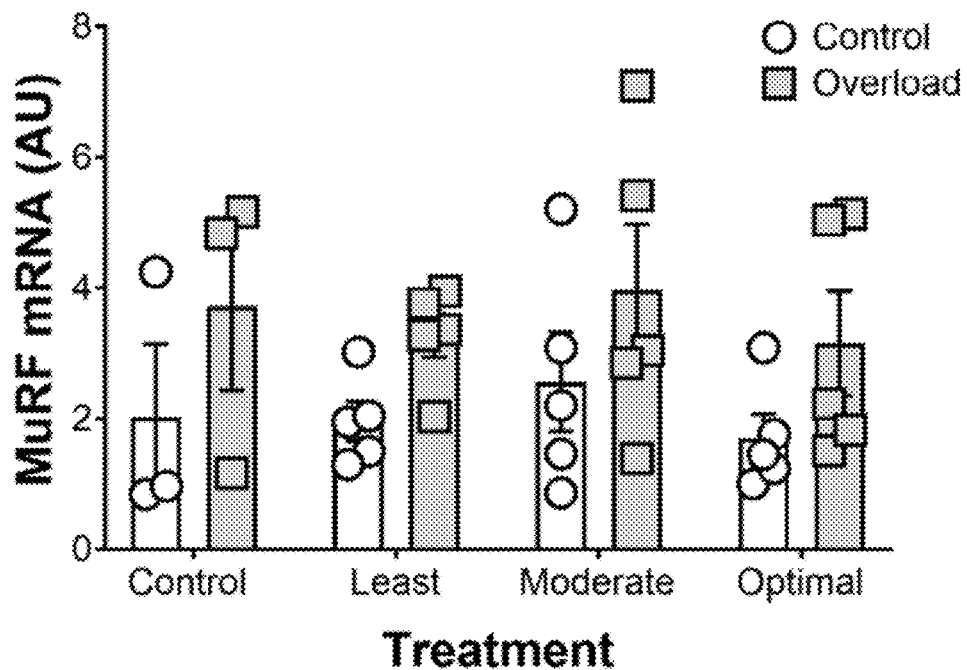
FIGS. 5A-5B. Markers of protein turnover with overload and natural product treatment.
Figure 5B:
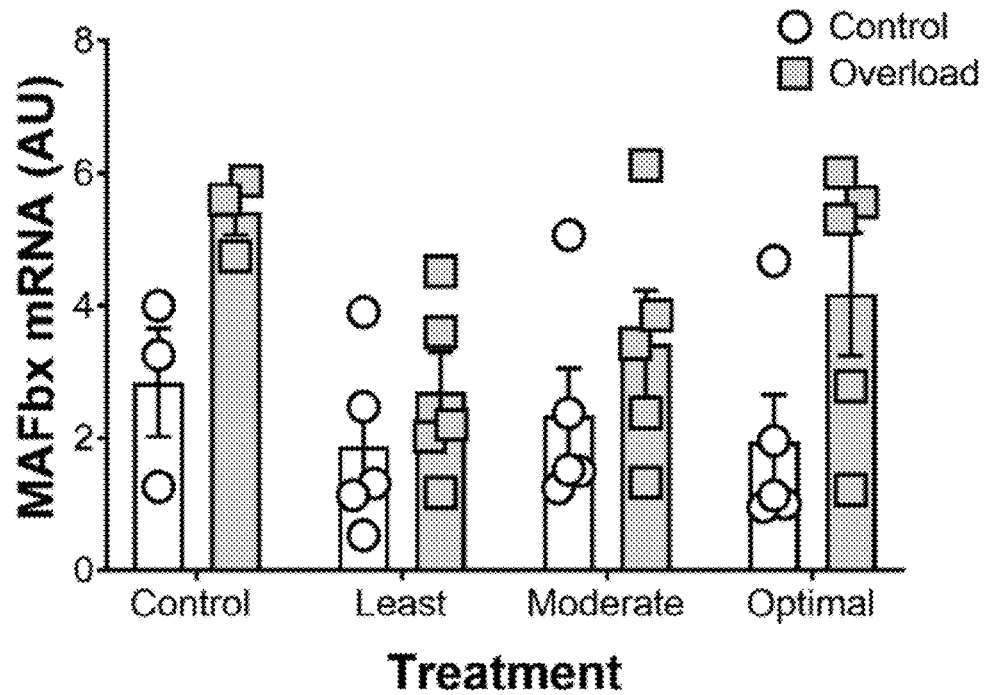

Since there was no effect of the natural products on protein synthesis, a quick measure of markers of protein turnover was made by measuring the expression of MuRF and MafBx. As has been reported previously, MuRF and MafBx expression tended to increase with overload and were not affected by the natural product treatment (FIG. 5).

Ribosomal Protein Acetylation

Figure 6A:
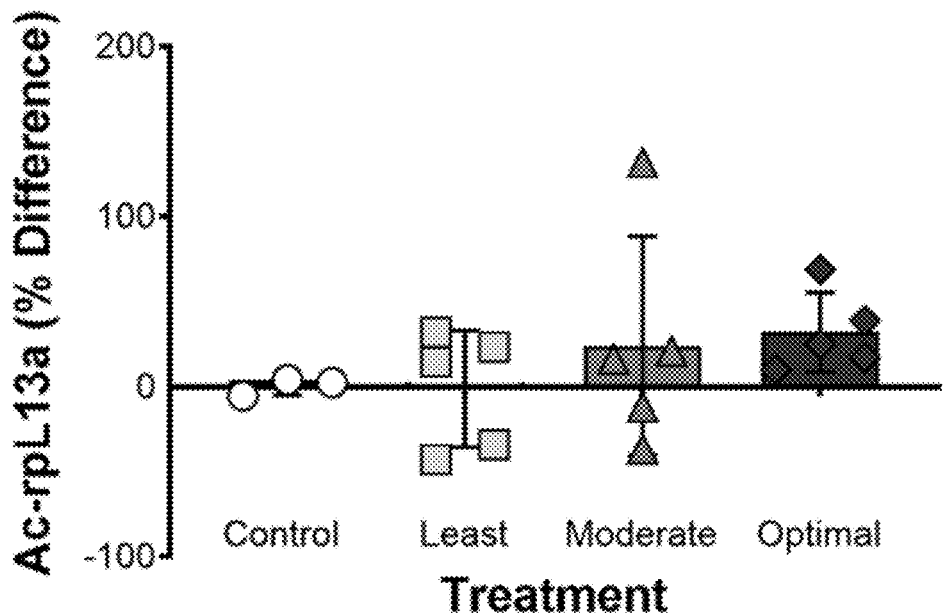
FIGS. 6A-6C. Acetylation of ribosomal proteins and regulators with overload and natural product treatment. To get an estimate of ribosomal acetylation, representative proteins from the large (L13A) (FIG. 6A) and small (S6) (FIG. 6B) ribosomal subunits were blotted following immunoprecipitation with an acetyl-lysine antibody.
Figure 6B:
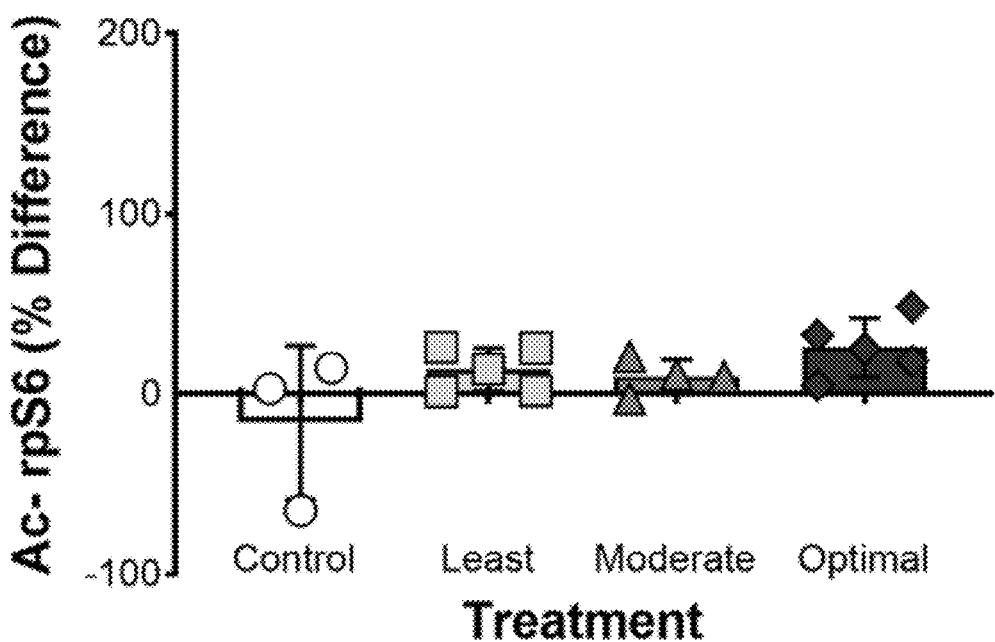
Figure 6C:
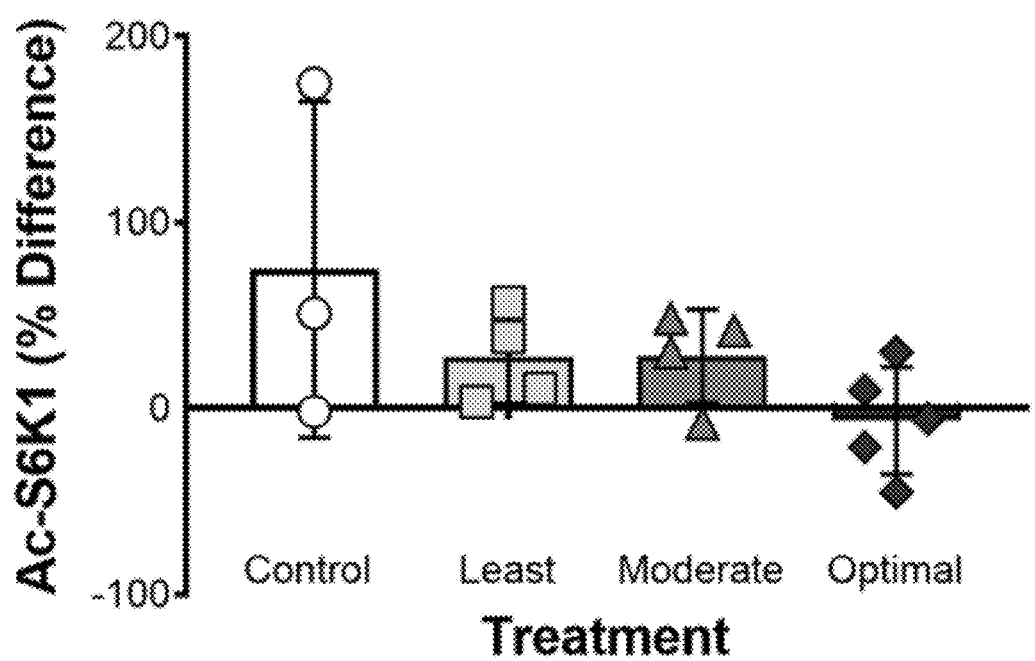

The ribosomal proteins are regulated by acetylation. Since SIRT1 is a deacetylase, the acetylation of proteins representative of the small and large ribosomal subunits was determined following immunoprecipitation. With optimization of the natural product cocktail, there was a trend for the acetylation of the ribosomal proteins to increase (FIGS. 6A-6B). By contrast, S6K1 acetylation tended to decrease with optimization of the natural product cocktail (FIG. 6C).

DISCUSSION

Here we show that several natural products have the ability to inhibit SIRT1 in an in vitro activity assay. Combining three of these natural products that are generally recognized as safe (GRAS), a Food and Drug Administration designation that a chemical added to food is considered safe by experts, and therefore exempt from the Federal Food, Drug, and Cosmetic Act food additive tolerance requirements, in the proper amounts results in a significant increase in muscle fiber hypertrophy following 14 days of overload. The significant increase in muscle fiber CSA was not the result of an increase in ribosomal mass. In fact, the optimal group showed significantly less 5'ETS and a strong trend towards lower ITS1 levels and total RNA, suggesting fewer ribosomes. The acetylation of ribosomal proteins tended to increase, suggesting that the increase in myofibrillar protein could be the result of an increase in ribosomal efficiency rather than capacity. Importantly, the natural product cocktail did not alter body mass or the weight of the heart and liver, suggesting that it has limited toxicity and may be useful in growing or maintaining muscle mass.

We have previously identified SIRT1 as one of a series of molecular breaks that limit the growth of muscle in response to extreme stimuli, such as synergist ablation. We hypothesized that the activation of SIRT1 would result in the deacetylation of TAF68, a component of the SL-1 transcription factor that drives the expression of 47S rRNA. Deacetylation of TAF68 has previously been shown to inhibit rRNA transcription and therefore ribosome mass. Since ribosome mass is thought to limit growth following synergist ablation (8, 11), we hypothesized that blocking SIRT1 would decrease TAF68 acetylation, increase the expression of rRNA, increase the capacity for protein synthesis, and allow greater skeletal muscle hypertrophy in response to overload. Consistent with this hypothesis, we have previously shown that knockout of SIRT1 increased, and overexpression of SIRT1 decreased, muscle hypertrophy in response to overload. Further, pharmacological inhibitors of SIRT1 could increase load-induced muscle hypertrophy, suggesting that acute treatments with a SIRT1 inhibitor could increase muscle hypertrophy in genetically normal animals. With this data, we sought to determine whether SIRT1 could be inhibited by natural products and produce the same improvement in growth.

Using the NatProd Collection, which includes 800 pure natural products and their derivatives, derived from plant, animal and microbial sources, we identified 45 compounds that inhibited the activity of SIRT1 towards p53 by greater than 65% at a concentration of 50 µM, and 35 compounds that inhibited SIRT1 by at least 20% inhibition at 5 µM. This represents a unique list of compounds, many of which are polyphenols, including quinones and flavonoids that inhibit SIRT1. The fact that the majority of the compounds that inhibited SIRT1 were polyphenols suggests that regulation of SIRT1 may be one reason that polyphenols have a significant impact on human health and disease prevention (13). We chose to focus on three of these polyphenols, epicatechin, epigallocatechin-3-gallate, and celastrol, because they had a history of use in human medical trials without complication, and have different chemical structures that might mean different degrees of digestion, absorption, delivery, and activity in muscle following ingestion.

Using an incomplete factorial design, we treated animals with different concentrations and combinations of natural products to create a model as to how each natural product contributes to the increase in muscle CSA following overload. Response surface plots were used to determine the relative importance of each component and their interaction with the other natural products in the cocktail (FIG. 1B). To validate the model, we chose three different combinations of the natural products based on their predicted effect on muscle fiber CSA following overload. An independent cohort of rats (n=5 per treatment) underwent synergist ablation and then received a daily gavage containing one of the three combinations of natural products, or the placebo control. The fact that the model prediction for the increase in fiber CSA was proportional to the measured change in CSA ($r^2$=0.9586), suggests that the model was valid and that the predicted combination of epicatechin, epigallocatechin-3-gallate, and celastrol was optimal for muscle hypertrophy.

The increase in muscle fiber CSA with the optimal combination of epicatechin, epigallocatechin-3-gallate, and celastrol resulted in a 61.5% increase in mean fiber CSA compared with ~4% in the control group; the increase in CSA in the optimal group was therefore more than 1500% that of the controls. This finding is striking for two reasons. First, as seen in FIG. 2F, the increase in muscle mass following overload was not proportional to the mean increase in fiber CSA. In fact, the mass of the muscle appeared to have to increase by ~80% before an increase in the mean fiber CSA was observed. However, we did not observe a significant increase in fiber number over that period. These data suggest that the majority of the increase in muscle mass that occurs following 14 days of functional overload is not due to an increase in average fiber CSA. In the plantaris muscle, there are regions of very big fibers and other regions of relatively small fibers. It is possible that the regional difference in fiber CSA negate any obvious effect on mean fiber area following overload. However, it is also possible that the muscle is growing in other ways. Following the removal of the soleus and gastrocnemius muscles, the ankle of the rat is held in a more dorsiflexed position, which would be expected to increase the resting length of the plantaris. We have preliminary data that indicates that one result of the shift in ankle position is that the plantaris muscle increases in length by approximately 10%. Others have recently made a similar suggestion in mice (10). These data suggest that the plantaris muscle may increase in mass as a result of functional overload in part through the addition of sarcomeres in series.

The finding that the optimal group had a 61.5% increase in mean fiber CSA compared with ~4% in the control group is also striking for the magnitude of the difference in hypertrophy obtained with the natural product cocktail. Other treatments that augment muscle hypertrophy, such as consuming leucine rich protein, have an effect size of ~5% (3). These data suggest that the mechanism underlying the effect of the natural product cocktail is distinct and likely rate limiting in skeletal muscle hypertrophy. One proposed limit to skeletal muscle hypertrophy in both mice and man is the capacity for protein synthesis; i.e., ribosome mass (8, 11, 18). To determine whether ribosome mass was increased in the animals fed the natural product cocktail we determined total RNA within the muscle. Contrary to our hypothesis, total RNA tended to increase less with the natural product cocktail than in the vehicle controls. In support of this observation, the rRNA spacers (ITS1 and 5'ETS) showed the same pattern, with the change in 5'ETS reaching statistical significance. These data suggest that even though the natural product cocktail increased hypertrophy, the improvement was not the result of an increase in translational capacity.

One possible explanation for the apparent increase in muscle protein without a concomitant rise in ribosome mass is an increase in translational efficiency. While there is a paucity of recent work on the role of acetylation of the ribosomal proteins and translational efficiency, early work showed that following hepatectomy, when protein synthesis rates increase to regenerate the tissue, the acetylation of the ribosomal proteins precedes the protein synthetic response (12). This suggests that acetylation of the ribosomal proteins may increase translational efficiency. Choudhary and colleagues identified 75 ribosomal proteins that were acetylated at a minimum of 136 locations (4). For the mitochondrial ribosome, proteins MRPL10 and 19 are deacetylated by the mitochondrial sirtuin SIRT3 (19). When SIRT3 is overexpressed, MRPL10 and 19 become deacetylated and this corresponds to a decrease in protein synthesis. When a catalytically inactive SIRT3 is used there is no change in acetylation or protein synthesis. Further, when SIRT3 is targeted with shRNA, acetylation and protein synthesis both increase (19). Lastly, ribosomes isolated from the liver of SIRT3 knockout mice show more protein synthesis per unit of ribosomal protein (19). Together, these data suggest that sirtuins can deacetylate ribosomal proteins and this corresponds to a decrease in translational efficiency. Consistent with these data, we show that our putative SIRT1 inhibiting natural product cocktail tends to increase the acetylation of two ribosomal proteins and this is associated with a greater change in protein synthesis (similar increases in puromycin) relative to total RNA or ribosomal biogenesis (SETS), suggesting improved translational efficiency.

Beyond the acetylation of ribosomal proteins, the cell size regulator S6K1 can also be acetylated (6, 7) and this decreases its ability to be phosphorylated by mTORC1 (9) and its ability to phosphorylate ribosomal protein s6 in mesangial cells (5, 9). The deacetylation of S6K1 can be catalyzed by either SIRT1 or 2 (9). Therefore, inhibition of SIRT1 would be expected to increase S6K1 acetylation and decrease Thr389 phosphorylation. Interestingly, in muscles treated for 14 days with presumed inhibitors of SIRT1, we observed a tendency for S6K1 acetylation and phosphorylation to both decrease. When trying to rectify our data with the existing literature, it is important to note that in the previous studies the effect of SIRT1 on S6K1 acetylation was performed in culture following 3 hours of treatment with the sirtuin inhibitor nicotinamide (9). It is also important to note that much of the in vitro study looked specifically at S6K1 acetylation at lysines 427, 484, 485, and 493. By contrast, the current work looked at total acetylation of S6K1 following immunoprecipitation. It is possible that longer periods of sirtuin inhibition in the presence of a growth stress would lead to the acetylation of 427, 484, 485, and 493 but deacetylation at other sites, resulting in the net deacetylation that was observed in the current study.

CONCLUSIONS

Using an in vitro assay, we have identified several natural products that can inhibit SIRT1 activity. By combining three of these inhibitors in vivo, we were able to develop a model for how different combinations contributed to muscle hypertrophy following overload. When validating the model, we discovered that the optimal combination of natural products could significantly increase muscle hypertrophy in response to loading even though it significantly decreased ribosome biogenesis and tended to decrease the rise in ribosome mass that occurs with overload. This suggests that the natural product described here may increase ribosome efficiency, possibly through the acetylation of ribosomal proteins, resulting in greater skeletal muscle hypertrophy.

REFERENCES

1. Baar K, Esser K. Phosphorylation of p70(S6k) correlates with increased skeletal muscle mass following resistance exercise. *Am J Physiol* 276: C120-C127, 1999.
2. Celis-Morales C A, Welsh P, Lyall D M, Steell L, Petermann F, Anderson J, Iliodromiti S, Sillars A, Graham N, Mackay D F, Pell J P, Gill J M R, Sattar N, Gray S R. Associations of grip strength with cardiovascular, respiratory, and cancer outcomes and all cause mortality: prospective cohort study of half a million UK Biobank participants. doi: 10.1136/bmj.k1651.
3. Cermak N M, Res P T, de Groot L C, Saris W H, van Loon L J. Protein supplementation augments the adaptive response of skeletal muscle to resistance-type exercise training: a meta-analysis. *Am J Clin Nutr* 96: 1454-64, 2012.
4. Choudhary C, Kumar C, Gnad F, Nielsen M L, Rehman M, Walther T C, Olsen J V, Mann M. Lysine Acetylation Targets Protein Complexes and Co-Regulates Major Cellular Functions [Online]. science.sciencemag.org/[2 Jul. 2019].
5. Das F, Maity S, Ghosh-Choudhury N, Kasinath B S, Ghosh Choudhury G. Deacetylation of S6 kinase promotes high glucose-induced glomerular mesangial cell hypertrophy and matrix protein accumulation. (2019). doi: 10.1074/jbc.RA118.007023.
6. Fenton T R, Gwalter J, Cramer R, Gout I T. S6K1 is acetylated at lysine 516 in response to growth factor stimulation. *Biochem Biophys Res Commun* 398: 400-405, 2010.
7. Fenton T R, Gwalter J, Ericsson J, Gout I T. Histone acetyltransferases interact with and acetylate p70 ribosomal S6 kinases in vitro and in vivo. *Int J Biochem Cell Biol* 42: 359-366, 2010.
8. Figueiredo V C, Mccarthy J J. Regulation of Ribosome Biogenesis in Skeletal Muscle Hypertrophy. (2019). doi: 10.1152/physiol.00034.2018.
9. Hong S, Zhao B, Lombard D B, Fingar D C, Inoki K. Cross-talk between Sirtuin and Mammalian Target of Rapamycin Complex 1 (mTORC1) Signaling in the Regulation of S6 Kinase 1 (S6K1) Phosphorylation. (2014). doi: 10.1074/jbc.M113.520734.
10. Jorgenson K W, Hornberger T A. The overlooked role of fiber length in mechanical load-induced growth of skeletal muscle. *Exerc Sport Sci Rev* 47: 258-259, 2019.
11. Kirby T J, Lee J D, England J H, Chaillou T, Esser K A, Mccarthy J J, Tj K, Lee C T, Ka E, Mccarthy J J. Blunted hypertrophic response in aged skeletal muscle is associated with decreased ribosome biogenesis. *J Appl Physiol* 119: 321-327, 2015.
12. Liew C C, Gornall A G. Acetylation of Ribosomal Proteins in Regenerating Rat Liver [Online]. pdfs.semanticscholar.org/0841/ 77fe07d19736f0e287aa1bdbd8ac23b9c5ff.pdf [2 Jul. 2019].
13. Pandey K B, Rizvi S I. Plant polyphenols as dietary antioxidants in human health and disease. *Oxid Med Cell Longev* 2: 270-8, [date unknown].
14. Rantanen T, Harris T, Leveille S G, Visser M, Foley D, Masaki K, Guralnik J M. Muscle Strength and Body Mass Index as Long-Term Predictors of Mortality in Initially Healthy Men [Online]. academic.oup.com/biomedgerontology/article-abstract/55/3NI168/2947973 [5 Jul. 2019].
15. Ruiz J R, Sui X, Lobelo F, Morrow J R, Jackson A W, Sjöström M, Blair S N. Association between muscular strength and mortality in men: prospective cohort study. *Br Med J* 337: a439, 2008.
16. Solomon J M, Pasupuleti R, Xu L, Mcdonagh T, Curtis R, Distefano P S, Huber L J. Inhibition of SIRT1 Catalytic Activity Increases p53 Acetylation but Does Not Alter Cell Survival following DNA Damage. *Mol Cell Biol* 26: 28-38, 2006.
17. Srikanthan P, Karlamangla A S. Muscle Mass Index As a Predictor of Longevity in Older Adults. *Am J Med* 127: 547-553, 2014.
18. Stec M J, Kelly N A, Many G M, Windham S T, Tuggle S C, Bamman M M, Bamman M M. First published February 9. *Am J Physiol Endocrinol Metab* 310: 652-661, 2016.
19. Yang Y, Cimen H, Han M-J, Shi T, Deng J-H, Koc H, Palacios O M, Montier L, Bai Y, Tong Q, Koc E C. NAD+-dependent Deacetylase SIRT3 Regulates Mitochondrial Protein Synthesis by Deacetylation of the Ribosomal Protein MRPL10. (2009). doi: 10.1074/jbc.M109.053421.

TABLE 1

Results of the SIRT1 inhibitor screen for those compounds described in the Example. The table shows the name of each compound, the percent inhibition at 5 μM or 50 μM, and the class of molecule that each compound belongs to.

| Compound Name | 50 μM | 5 μM | Class |
| --- | --- | --- | --- |
| Celastrol | 100 | 101 | Quinone-Methide |
| Dihydrocelastrol | 99 | 84 | Quinone |
| Epigallocatechin-3-monogallate | 99 | 72 | Polyphenol |
| Epicatechin monogallate | 99 | 66 | Flavonoid |

TABLE 2

Inhibitor compounds and the dose used during the validation study

| Compound Name | Optimal Dose | Average Dose | Least Dose |
| --- | --- | --- | --- |
| Celastrol | 0.5 | 0.2 | 0.435 |
| Epigallocatechin-3-Monogallate | 20 | 14 | 6 |
| Epicatechin Monogallate | 0.7 | 0.7 | 1.3 |

List of doses (mg/kg/day) of each inhibitor used in the validation study

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A composition for enhancing muscle growth in a mammal undergoing muscle loading, the composition comprising epicatechin, epigallocatechin-3-monogallate, and celastrol or dihydrocelastrol, wherein the relative weight ratio of the epicatechin, epigallocatechin-3-monogallate, and celastrol or dihydrocelastrol in the composition is about 0.7:20:0.5, respectively.

2. A method of enhancing skeletal muscle growth in a mammal undergoing muscle loading, comprising administering to the mammal a composition of claim 1.

3. The method of claim 2, wherein the composition:
   (a) results in an increase in the muscle fiber cross-sectional area of at least one skeletal muscle in the mammal;
   (b) does not substantially alter the body mass or the weight of the heart or of the liver in the mammal;
   (c) reduces the activity of SIRT1 in one or more muscles of the mammal; and/or
   (d) increases the acetylation of one or more ribosomal proteins in one or more muscles of the mammal.

4. The method of claim 2, wherein the composition is formulated as a nutritional supplement or food additive.

5. The method of claim 2, wherein the composition is formulated and administered such that the mammal receives about 0.7 mg/kg/day of epicatechin.

6. The method of claim 2, wherein the composition is formulated and administered such that the mammal receives about 20 mg/kg/day of epigallocatechin-3-monogallate.

7. The method of claim 2, wherein the composition is formulated and administered such that the mammal receives about 0.5 mg/kg/day of celastrol.

8. The method of claim 2, wherein the composition is formulated and administered such that the mammal receives about 0.7 mg/kg/day of epicatechin, about 20 mg/kg/day of epigallocatechin-3-monogallate, and about 0.5 mg/kg/day of celastrol.

9. The composition of claim 1, wherein the composition is formulated as a nutritional supplement or food additive.

10. The composition of claim 9, wherein the nutritional supplement or food additive is a pill, tablet, capsule, liquid, powder, energy bar, protein bar, or gummy.

11. The composition of claim 1, wherein the composition is formulated such that the mammal receives about 0.7 mg/kg/day of epicatechin.

12. The composition of claim 1, wherein the composition is formulated such that the mammal receives about 20 mg/kg/day of epigallocatechin-3-monogallate.

13. The composition of claim 1, wherein the composition is formulated such that the mammal receives about 0.5 mg/kg/day of celastrol.

14. The composition of claim 1, wherein the composition is formulated such that the mammal receives about 0.7 mg/kg/day of epicatechin, about 20 mg/kg/day of epigallocatechin-3-monogallate, and about 0.5 mg/kg/day of celastrol.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 1
tccgttttct cgctcttccc                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccggagagat cacgtaccac                                              20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acgcacgcct tcccagagg                                               19

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgcgtctcgc ctggtctctt g                                            21
```